(12) United States Patent
Shibuya

(10) Patent No.: US 6,589,219 B1
(45) Date of Patent: Jul. 8, 2003

(54) DISPOSABLE BODY FLUID FILTER UNIT, DISPOSABLE BODY FLUID SUCKING DEVICE, AND BODY FLUID SUCKING SOURCE

(76) Inventor: Ichiro Shibuya, 4-5, Saigawa 3-Chome, Otsu-shi, Shiga 520-0002 (JP)

( * ) Notice: Subject to any disclaimer, the term of this patent is extended or adjusted under 35 U.S.C. 154(b) by 0 days.

(21) Appl. No.: 09/914,410
(22) PCT Filed: Nov. 15, 2000
(86) PCT No.: PCT/JP00/08064

§ 371 (c)(1),
(2), (4) Date: Aug. 28, 2001

(87) PCT Pub. No.: WO01/36020

PCT Pub. Date: May 25, 2001

(30) Foreign Application Priority Data

Nov. 15, 1999 (JP) .............................. 11-323515

(51) Int. Cl.[7] .................................. A61M 1/00
(52) U.S. Cl. .................. 604/319; 128/205.19
(58) Field of Search ................. 604/317–319, 604/252, 320, 333, 19, 27, 35; 128/200.26, 205.19, 207.14

(56) References Cited

U.S. PATENT DOCUMENTS

| 4,747,843 A | * | 5/1988 | Felix et al. ................ 604/318 |
| 4,995,386 A | * | 2/1991 | Ng ........................ 128/205.19 |
| 5,098,418 A | * | 3/1992 | Maitz et al. ............... 604/141 |
| 6,142,982 A | * | 11/2000 | Hunt et al. ............... 604/313 |
| 6,352,525 B1 | * | 3/2002 | Wakabayashi ............... 604/19 |

* cited by examiner

*Primary Examiner*—Weilun Lo
*Assistant Examiner*—Linh Truong
(74) *Attorney, Agent, or Firm*—Milde & Hoffberg, LLP

(57) ABSTRACT

A disposable body fluid filter unit 10 of the present invention comprises a suction inlet 14 connected to a suction tube 20 for suctioning body fluids 100; a collection chamber 18 for storing the body fluids 100 sucked in together with air after being separated from air; a filter 12 for allowing introduced air to pass through; and a collection inlet 16 communicating with a suction source 24, wherein the suction inlet 14 is positioned at one end of the substantially cylindrical-shape collection chamber 18, the filter 12 is positioned at the other end that is opposite to the one end, and a collection piper 23 is provided for guiding air from the chamber 18 to the collection inlet 14 through the filter 12.

14 Claims, 20 Drawing Sheets

(a)

(b)

DISPOSABLE BODY FLUID FILTER UNIT, DISPOSABLE BODY FLUID SUCKING DEVICE, AND BODY FLUID SUCKING SOURCE

FIELD OF THE INVENTION

The present invention relates to a disposable suction device used for removing phlegm and nasal mucus caught in person's throat and nose.

BACKGROUND OF THE INVENTION

Since patients whose strength is declined and elderly people may be unable to spit out phlegm caught in their throats by themselves, they have their phlegm removed by medical treatment facilities and helpers. Similarly, when infants have a plugged nose, their parents remove nasal mucus by their mouths. Although suction sources such as vacuum pumps were used for removing body fluids in medical treatment facilities, there were problems, such as difficult movement due to their large-size suction devices or troublesome work in cleaning and disinfecting suction pipes and spit boxes after use. In addition, there was always a risk of being infected when. reusing the suction devices, even if the devices had been cleaned and disinfected.

On the other hand, a method for sucking out phlegm by a user's mouth using suction tubes has been taken in ordinary households without such suction devices. Accordingly, serious hygienic and mental problems that the family members might become infected with the disease of the patients by the phlegm and the like having drawn into their mouths have been raised.

The inventors of the present invention have been succeeded in developing a disposable body fluid filter unit and a body fluid suction device free from cleaning and disinfection after repeated studies, which are capable of being easily used at anywhere because of convenient portable type, and perfect for collecting body fluids such as phlegm and nasal mucus.

DISCLOSURE OF THE INVENTION

A disposable body fluid filter unit according to the present invention for removing body fluids such as phlegm and nasal mucus is so configured that air flows through a suction inlet connected to a suction tube for suctioning the body fluids, a collection chamber, a filter, and a collection inlet communicating with a suction source in the order named to suction the body fluids.

In the filter unit, a suction pipe for guiding air from the suction inlet to the collection chamber passes through the filter.

The filter is positioned between the suction inlet and the collection inlet.

In the filter unit, a shielding member having a body fluid shielding portion in the shape being in conformance with the shape of inner walls of the collection chamber disposed around the shielding member and a ventilation section formed near the central portion is provided between the collection chamber and the filter.

The disposable body fluid filter unit according to the present invention for removing body fluids such as phlegm and nasal mucus caught in person's throat and nose comprises a suction inlet connected to a suction tube for suctioning the body fluids; a collection chamber for storing the body fluids suctioned from the suction inlet; a filter for allowing air or body fluids within the collection chamber to pass through; and a collection inlet communicating with a suction source, wherein the suction inlet is positioned at one end of the collection chamber, the collection inlet is positioned at the other end that is opposite to the one end, and the filter is positioned between the collection chamber and the collection inlet.

The filter unit further comprises a collection pipe for guiding air from the collection chamber to the collection inlet through the filter which juts into the collection chamber.

The collection pipe juts out of the filter into the central portion of the collection chamber and an end of a jutting portion of the collection pipe is positioned near the central portion of the collection chamber.

The filter unit further comprises a suction pipe for guiding body fluids from the suction inlet to the collection chamber.

The suction pipe juts into the collection chamber.

A jutting portion of the suction pipe has a non-return valve on its end.

In the filter unit, a collection chamber is at least small enough to conceal in a palm of a person's hand.

A disposable body fluid suction device according to the present invention comprises the above-mentioned filter unit, wherein a suction tube is connected at least to the suction inlet.

In the suction device, a nozzle having an air inhalation system is connected to the end of the suction tube.

The collection inlet is of a shape that allows a user to hold the inlet in his or her mouth.

A suction source according to the present invention for introducing air from a collection inlet of a body fluid filter unit for removing body fluids such as phlegm and nasal mucus caught in person's throat and nose comprises a pump for sucking air; and an outer box for having the pump therein, wherein the outer box can be suspended by engaging a curved hook extending to an end with a bar-like member.

The suction source according to the present invention for introducing air from the collection inlet of the filter unit for removing body fluids such as phlegm and nasal mucus caught in person's throat and nose comprises a pump for sucking air; and an outer box having the pump therein, wherein the outer box has a curved mounting section extending to an end, where a substantially cylindrical shaped body fluid filter unit is accommodated on its side.

The suction source according to the present invention for introducing air from the collection inlet of the filter unit for removing body fluids such as phlegm and nasal mucus caught in person's throat and nose comprises a pump for sucking air; an outer box having the pump therein; and a tank for dividing collected body fluids into body fluids and air.

BRIEF DESCRIPTION OF THE DRAWINGS

FIG. 16(a) is a two-layer structure and FIG. 16(b) is an example of a shape with circular base and jutting sidewalls.

FIG. 22(a) is a front view, FIG. 22(b) is a bottom plan view. FIG. 22(c) is an A=A cross-sectional view shown in FIG. 22(b).

DESCRIPTION OF THE PREFERRED EMBODIMENTS

A preferred embodiment of the disposable body fluid filter unit and the body fluid suction device according to the present invention will now be described in detail on the basis of the accompanying drawings.

Figure 1:
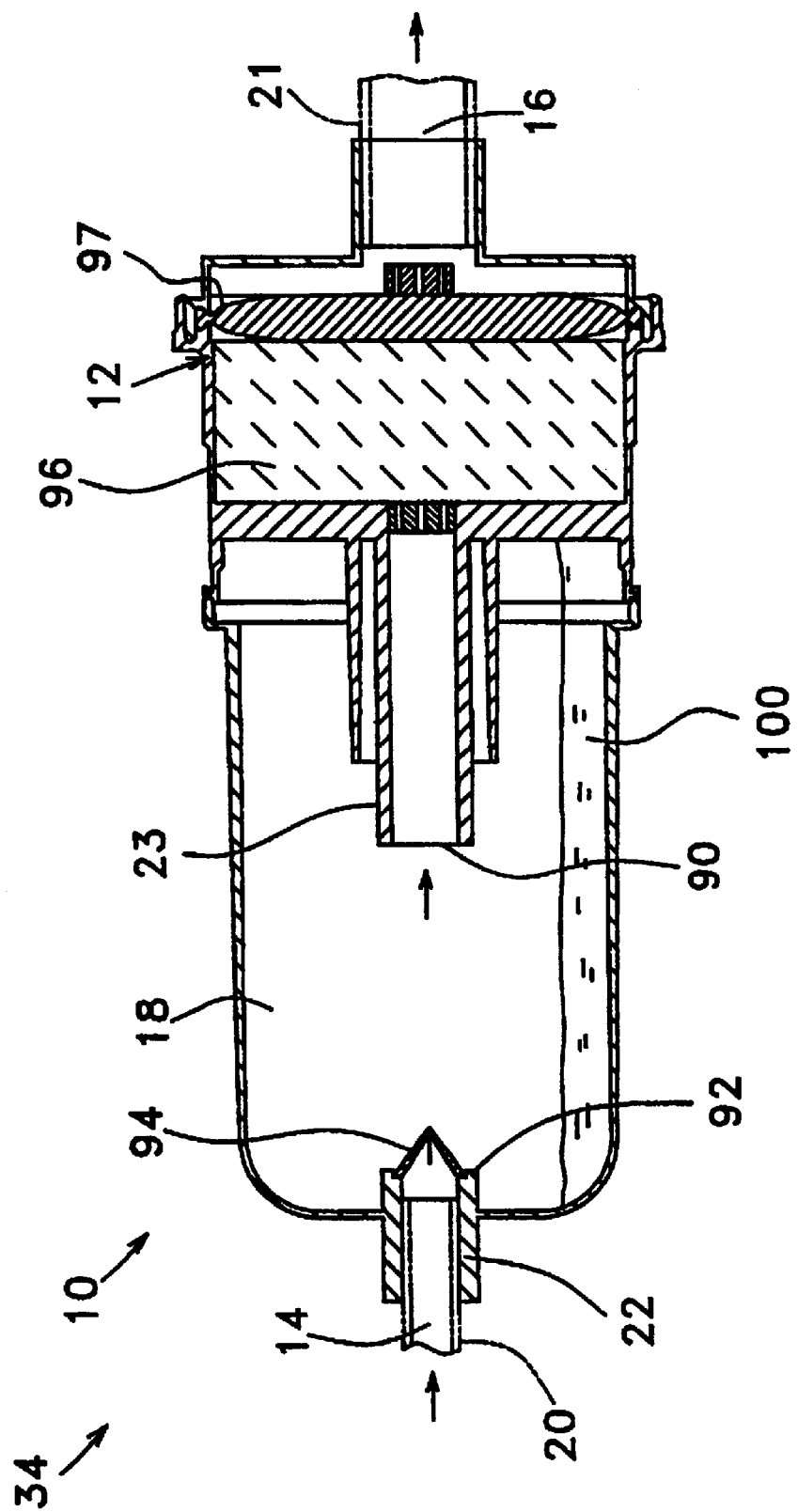
FIG. 1 is a front cross-sectional view showing an example of a filter unit according to the present invention.

FIG. 1 shows an example of a particularly preferred embodiment of a filter unit according to the present invention. A filter unit 10 shown in FIG. 1 comprises a suction inlet 14 connected to a suction tube 20 for collecting body fluids 100; a sealed collection chamber 18 for storing the body fluids 100 after separating the body fluids 100 collected along with air from the air; and a filter 12 for allowing introduced air to pass through; and a collection inlet 16 communicating with a suction source 24.

More particularly, in the filter unit 10, the suction inlet 14 is positioned at one end of the substantially cylindrical-shape collection chamber 18, the collection inlet 16 is positioned at the other end that is opposite to the one end, and the filter 12 is positioned between the chamber 18 and the collection inlet 16. In the body fluid filter unit according to the present invention, a collection pipe 23 is provided to guide air from the chamber 18 to the collection inlet 14 through the filter 12 and juts out of the filter 12 into the central portion of the chamber 18, wherein an end 90 of a jutting portion of the pipe 23 is positioned near the central portion of the chamber 18. The pipe 23 is constructed in a double tube state to make it difficult for the body fluids 100 to draw into the pipe 23 or to reduce kinetic energy of body fluids by absorption. Further, a suction pipe 22 juts into the chamber 18 so that the pipe 22 may guide the fluids 100 from the suction inlet 14 to the chamber 18. Furthermore, a jutting portion of the pipe 22 has a non-return valve 94 on its end 92.

Figure 6:
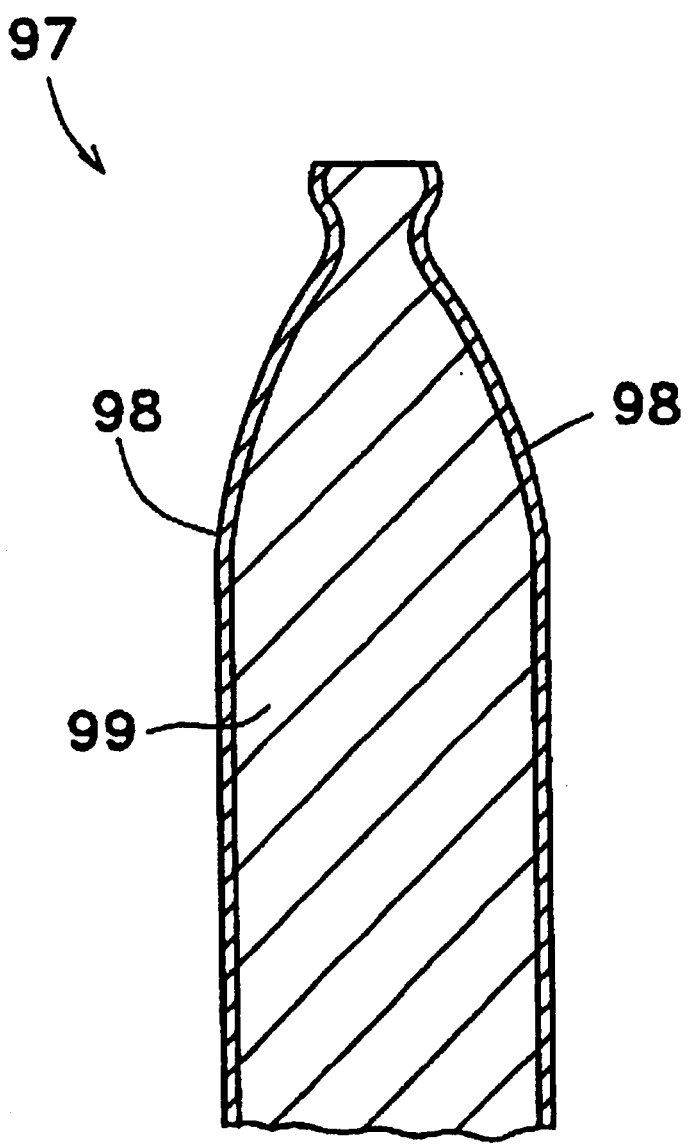
FIG. 6 is a front cross-sectional view of a sterilizing filter of the filter unit shown in FIG. 1.

The filter 12 is positioned between the collection pipe 23 and the collection inlet 16, and is so constructed that air to be fed from the collection chamber 18 to the filter 12 through the collection pipe 23 may be fed to the inlet 16 after being cleaned by the filter 12. In addition, when the body fluids 100 are included in air to be fed from the collection chamber 18 to the filter 12 through the pipe 23, the filter 12 collects the fluids 100, so that only clean air is fed to the inlet 16. If the fluids 100 are included in air to be fed to the filter 12, the filter 12 comprises a sponge 96 for absorbing the fluids and a sterilizing filter 97 for separating microorganisms by collecting microorganisms to prevent them from passing through the filter 97. As shown in FIG. 6, the filter 97 comprises a lamination sandwiching a sponge 99 between two HEPA filters (High Efficiency Particulate Air Filters) 98. The HEPA filters 98 are capable of collecting 0.3 $\mu$m-particles with the efficiency of 99.97% or higher. Since 2 pieces of the HEPA filters 98 are used, the filter 97 is capable of collecting 0.3 $\mu$m-particles with the efficiency of 100−(100−99.97)×(100−99.97)=99.9991% or higher.

The collection chamber 18 is small enough to conceal in a palm of a human hand. And then the collection chamber 18 is so configured that the inside of the chamber 18 may be invisible from the outside by gripping it and the body fluids 100 to pass through the chamber 18 are invisible from the outside. More specifically, the length of the substantially cylindrical-shape filter unit 10 is within the range of 100 mm to 110 mm. The diameter of a cross-sectional circle of the substantially cylindrical-shape collection chamber 18 is within the range of 35 mm to 45 mm. The reason for hiding the collection chamber by hand is to avoid any unpleasant feelings or a feeling of repulsion that the patient, the caregiver, and the patient's family or visitors may have. Further, that is because of holding the patient's zest for life, self-help, and fighting spirit against the disease. The chamber 18 can be quickly and easily thrown away by downsizing.

Figure 2:
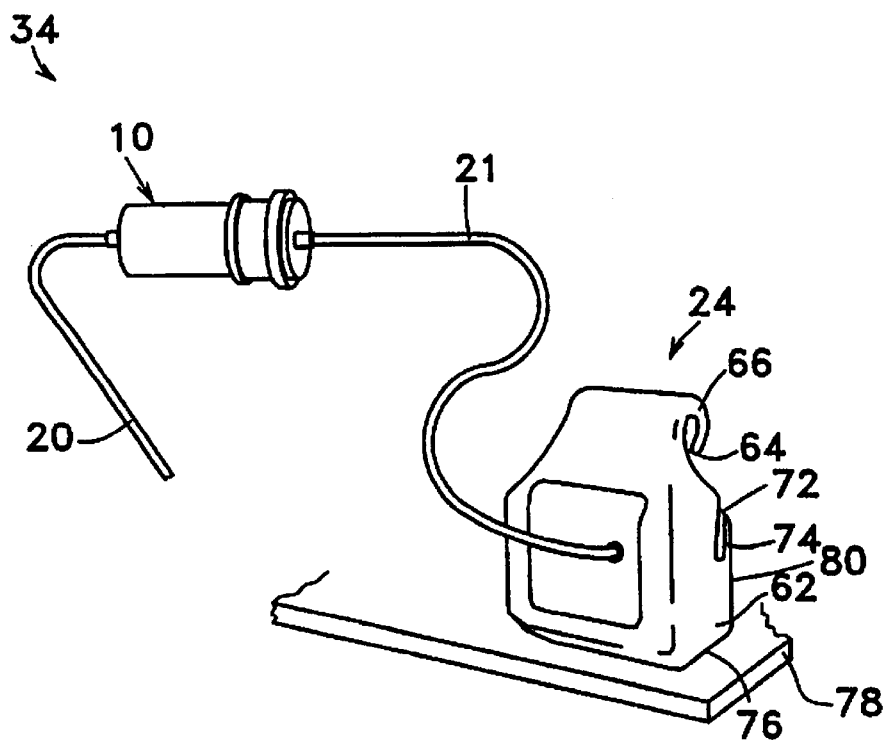
FIG. 2 is a perspective view showing the filter unit shown in FIG. 1 and a suction source according to the present invention.
Figure 3:
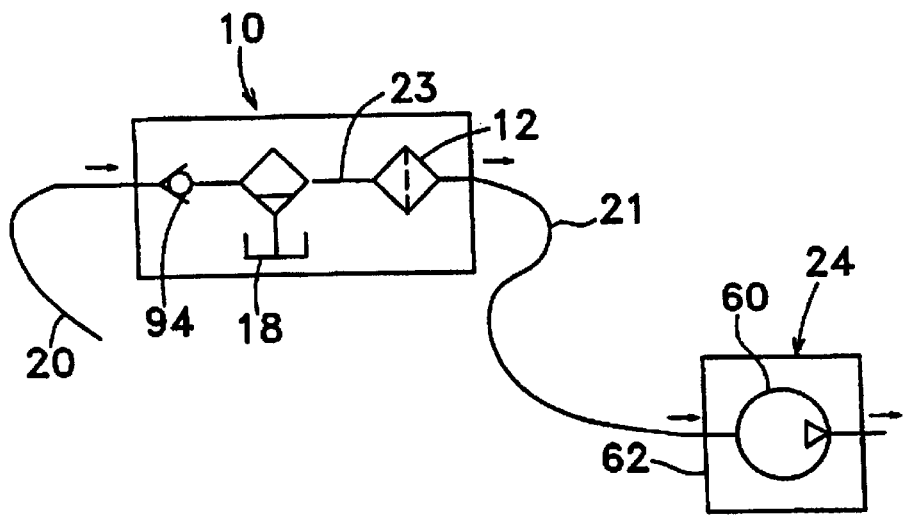
FIG. 3 is a pipe arrangement view showing the filter unit shown in FIG. 1 and a suction source according to the present invention.
Figure 4:
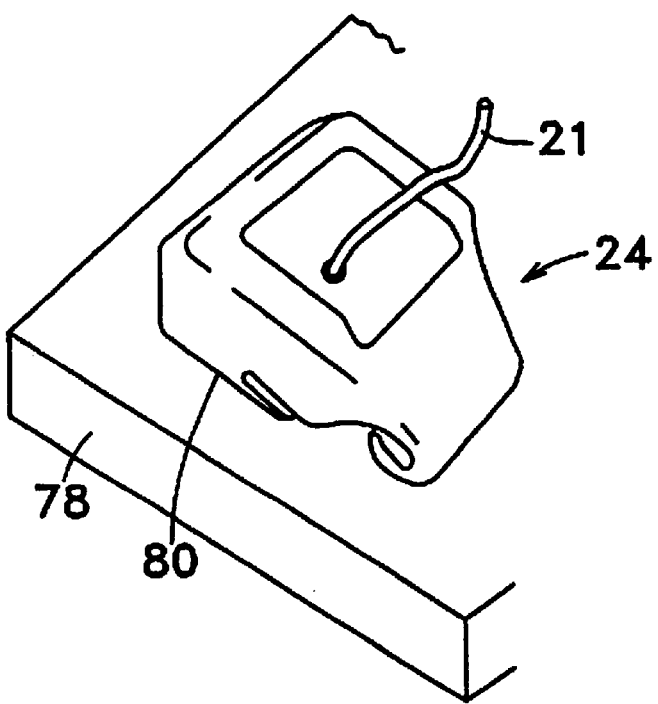
FIG. 4 is a perspective view showing the suction source shown in FIG. 2 in another using condition.
Figure 5:
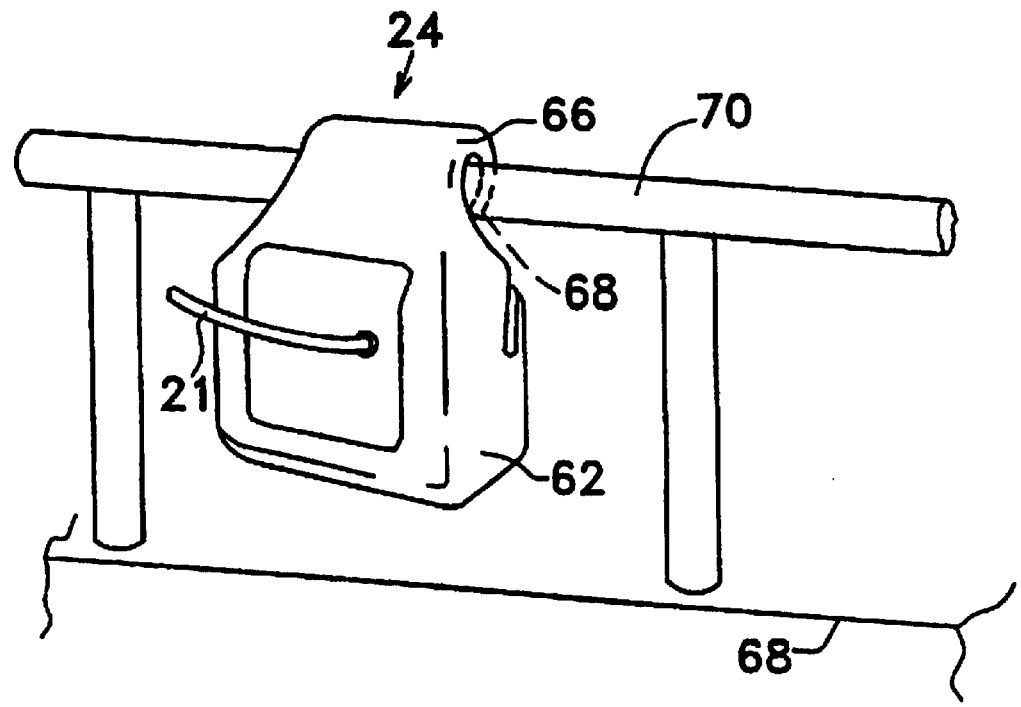
FIG. 5 is a perspective view showing the suction source shown in FIG. 2 in still another using condition.

A suction source 24 comprises, as shown in FIG. 3, a pump 60 for sucking air and an outer box 62 having the pump 60 therein, and is so configured that air may be introduced from a collection tube 21 by the operation of the pump 60. The box 62 is composed of one component including a hook 66 extending to an end 64. As shown in FIG. 5, the box 62 is configured so as to fix the suction source 24 to a bed 68 by fitting the hook 66 into a fence (bar-like member) 70 of the bed 68, which enables the hanging of the suction source 24. Further, the box 62 is composed of one component including a curved mounting section 74 extending to an end 72 and is configured so as to accommodate the substantially cylindrical-shape filter unit 10 on its side in the mounting section 74. The box 62 has, furthermore, a planate bottom 76, and as shown in FIG. 2, is so configured that the bottom 76 may closely come in contact with and be fixed to a desk 78. In addition, the outer box 60 has a planate rear 80, and as shown in FIG. 4, is so configured that the rear 80 may closely come in contact with and be fixed to the desk 78. This suction source 24 may be used in the oblique direction, or the like.

When such body fluid filter unit 10 and suction source 24 are used, a body fluid suction device 34 is assembled by pressing a suction tube 20 into the suction inlet 14 of the filter unit 10, as well as pressing the collection tube 21 connected to the suction source 24 into the collection inlet 16. Catheters made of sterilized PVC (polyvinyl chloride) available in the market are generally used as the suction tube 20 and the collection tube 21.

Subsequently, body fluids 100 such as phlegm and nasal mucus are sucked into the suction tube 20 by putting an end of the tube 20 into the user's nose or mouth to the throat or the trachea to operate the pump 60 of the suction source 24. The fluids 100 suctioned in the tube 20 are guided from the tube 20 to the suction inlet 14 and is stored in the collection chamber 18 after passing through a non-return valve 94. As shown in FIG. 3, the collection chamber 18 acts as a tank for dividing into three: the body fluids 100; mixed body fluids 100 formed by mixing the body fluids with air; and air or a drain. The non-return valve 94 prevents the fluids 100 from returning.

On the other hand, air introduced into the collection chamber 18 is guided from the collection pipe 23 to the pump 60 through the filter 12 and the collection tube 21 and is discharged from the pump 60. Air introduced into the collection chamber 18 is guided to the collection tube 21 while removing bacteria included in the air with the HEPA filters 98 of the filter 12. Even if the body fluids 100 draw into the collection pipe 23, there is no possibility of the body fluids 100 draw into the collection tube 21 because of being absorbed in the sponge 96. Accordingly, even if the collection tube 21 has been used for a plural number of patients without throwing away the tube 21, the patients would not have unpleasant feelings because of no remainder of the other patients' body fluids in the tube 21.

Figure 7:
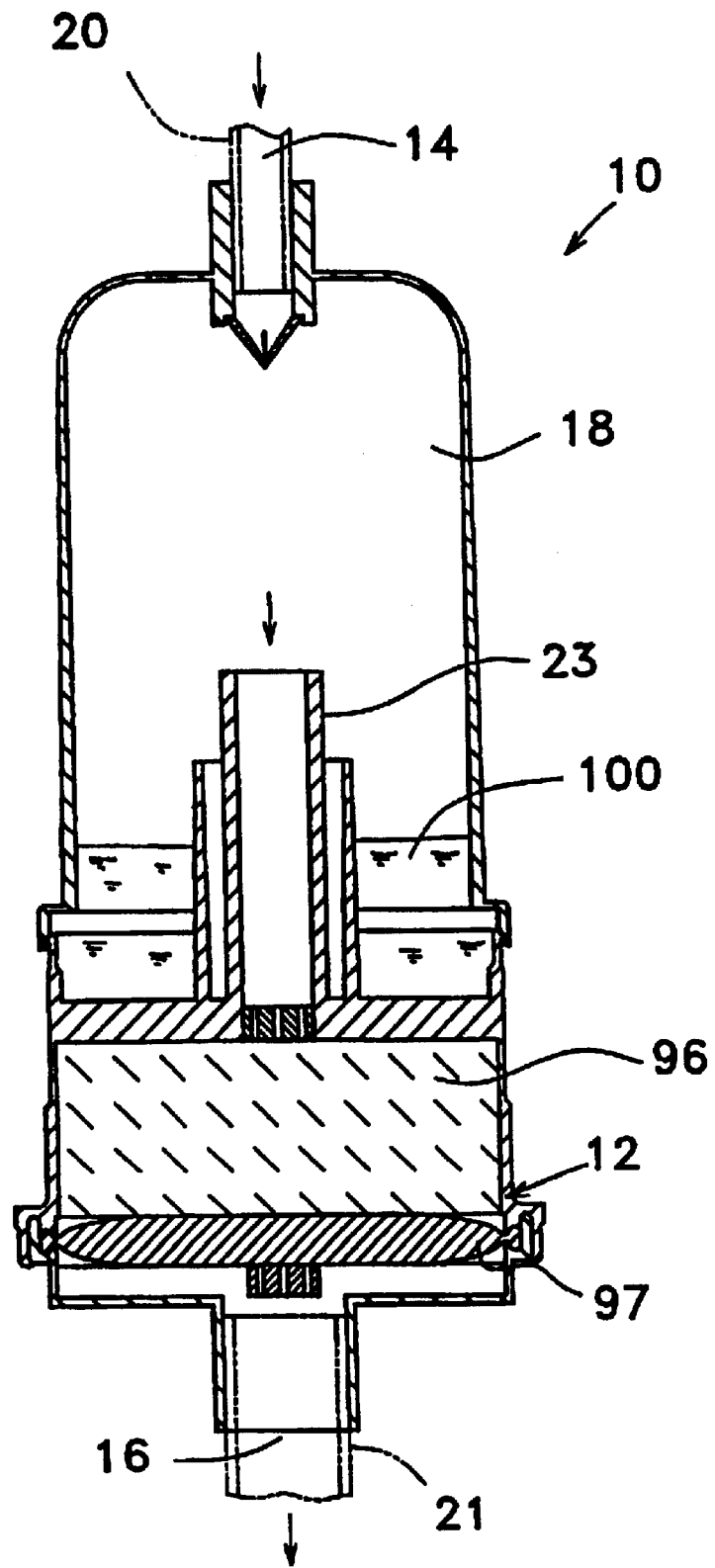
FIG. 7 is a perspective view showing the filter unit shown in FIG. 1 in a further using condition.
Figure 8:
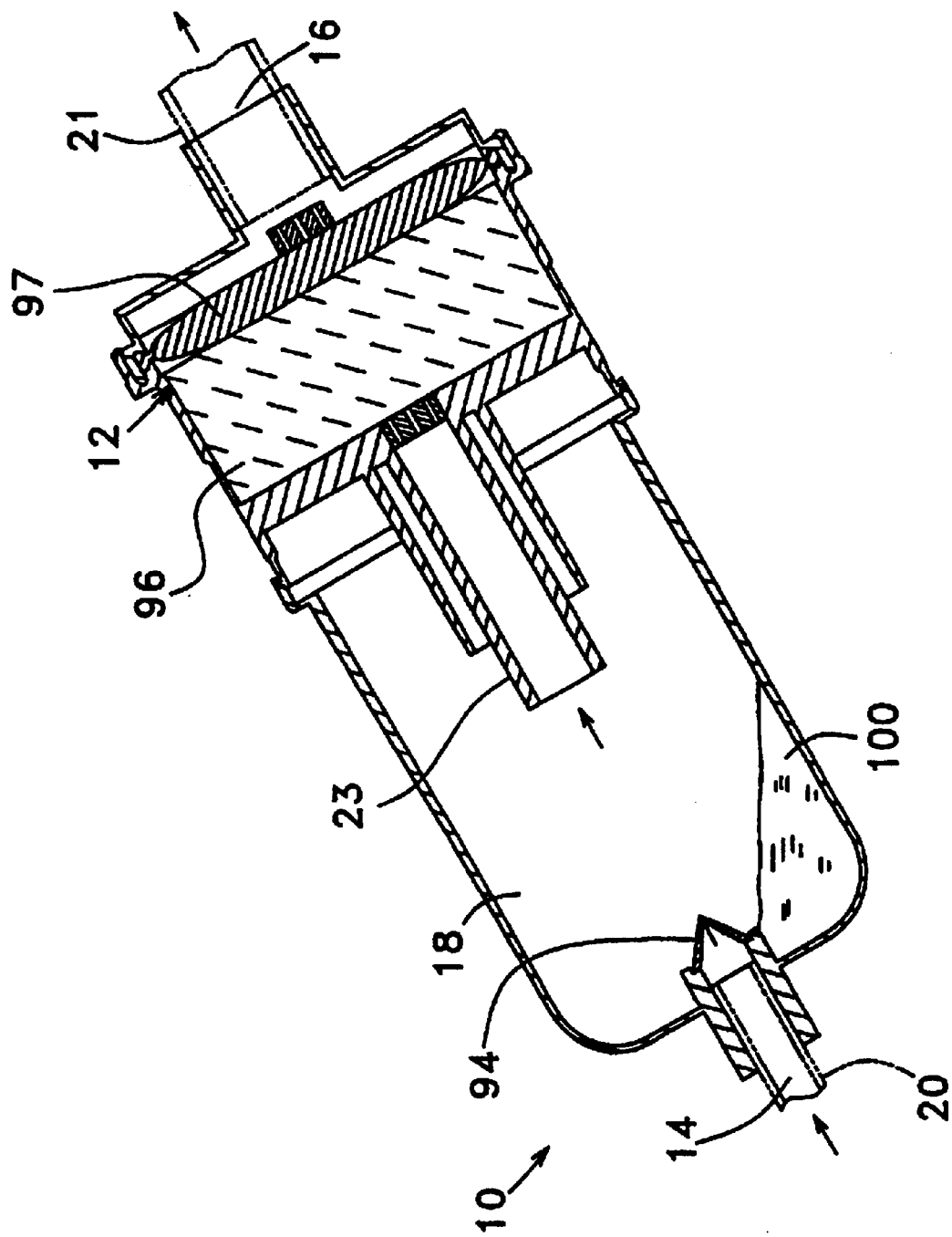
FIG. 8 is a perspective view showing the filter unit shown in FIG. 1 in a still further using condition.

The collection pipe 23 juts out of the filter 12 into the central portion of the collection chamber 18 with the end 90 of the jutting portion positioned near the central portion of the collection chamber 18. For this reason, there is a low possibility of the body fluids 100 drawing into the collection pipe 23 due to the storage of the fluids 100 at the bottom of the sideway positioned collection chamber 18, as far as the amount of the fluids 100 is not too large, when the body fluid filter unit 10 is used in a sideway position as shown in FIG. 1. Moreover, the suction pipe 22 juts into the chamber 18 and the non-return valve 94 is disposed at the end 92 of the jutting portion of the pipe 22, so that there is no possibility of the fluids 100 drawing into the pipe 22 due to no contact with the non-return valve 94. In both cases when the filter unit 10 is used, as shown in FIG. 7, with the suction inlet 14 turning upward in a upright position and when the filter unit 10 is used, as shown in FIG. 8, with the suction inlet 14 turning downward in an oblique position, few admission of the fluids 100 into the pipe 23 occurs due to the same theory, so that there is no possibility of the fluids 100 drawing into the pipe 22.

Thus, once the body fluid filter unit 10 has been used and the body fluids 100 have been stored in the collection chamber 18 at a predetermined amount, the filter unit 10 and the suction tube 20, and the like are thrown away.

With the use of this body fluid filter unit 10, it is rare that the body fluids 100 draw into the collection pipe 23 and the amount of the body fluids 100 which exceptionally draw into the pipe 23 is very little, so that all of the fluids 100 drawing into the pipe 23 can be absorbed in the sponge 96. This avoids the fluids 100 from being sucked up to the suction source 24, passing through the collection tube 21 to prevent the breakdown of the suction source 24 caused by the admission of the fluids 100 into the pump 60. In addition, it becomes possible for a caregiver to suction body fluids by holding the tube 21 in his or her mouth without the suction source 24 due to no admission of the fluids 100 into the tube 21. Furthermore, this filter unit 10 enables the caregiver to prevent the infection due to effective sterilization using the filter 12 equipped with two HEPA filters 98, even if the caregiver suctions body fluids by holding the tube 21 in his or her mouth.

As shown in FIG. 1, the body fluid filter unit 10 is capable of suctioning body fluids in the state of fixing to the hook 74 of the suction source 24 in a sideway position, so that the filter unit 10 is capable of suctioning body fluids in a stable state. It is, therefore, possible to avoid the body fluids 100 from being sucked up to the suction source 24 after passing through the collection tube 21 by preventing the body fluids 100 from drawing into the collection pipe 23.

One embodiment of the body fluid filter unit and the body fluid suction device of the present invention has been described with reference to accompanying drawings, however, the present invention is not limited to this embodiment.

For example, a ULPA (Ultra Low Penetration Air) filter may be used as an alternative to the HEPA filters 98 for sterilizing filter 97 equipped with the body fluid filter unit 10 shown in FIG. 1. When compared to the HEPA filters, the ULPA filters are brittler and easy to cause waste in addition to their high price. The ULPA filters can, however, collect 0.1 μm-particles at the efficiency of 99.999% or higher.

For the body fluid filter unit 10 shown in FIG. 1, the filter 12 may be composed of the sponge 96 only excluding the sterilizing filter 97. Furthermore, a sponge may be used as an alternative to the sterilizing filter 97. In addition, a high polymer absorbent material may be used as a component for the filter 12.

If the filter 12 is composed of a sponge only, the filter 12 can be used for suctioning oral body fluids at the time of brushing teeth when excessive consideration of sterilization of body fluids is not necessary. If a high polymer absorbent material or a sponge is used, it is possible to recognize the time when the filter 12 should be thrown away by visually checking the swelling of the high polymer absorbent material or the sponge caused by the absorption of body fluids into the high polymer absorbent material or the sponge. Further, the time when the filter 12 should be thrown away can be recognized by recognizing air permeability of the material or the sponge has been lowered due to absorption of body fluids into the material or the sponge. The filter 12 may be composed of the filter 97 only excluding the sponge 96. The filter 97 may be composed of the HEPA filters only. Furthermore, the number of the HEPA filters of the filter 97 in the filter 12 is not limited to 2 as shown in FIG. 6, but at least one or two or more HEPA filters may be used.

The length of the substantially cylindrical-shape body fluid filter unit 10 shown in FIG. 1 may be within the range of 110 mm to 120 mm and 120 mm to 130 mm. Or the length of the filter unit 10 may be within the range of 90 mm to 100 mm, 80 mm to 90 mm, 70 mm to 80 mm, 60 mm to 70 mm, and 50 mm to 60 mm. The diameter of the cross-sectional circle of the substantially cylindrical-shape collection chamber 18 may be within the range of 45 mm to 55 mm and 55 mm to 65 mm. Further, the diameter of the cross-sectional circle may be within the range of 25 mm to 35 mm and 15 mm to 25 mm.

For the body fluid filter unit 10 shown in FIG. 1, a suction source for operating the filter unit 10 is not limited to the suction source 24 shown in FIG. 5. More particularly, the shape of the suction source's outer box is not particularly limited, if the suction source can introduce air from the filter unit 10.

The body fluid filter unit 10 shown in FIG. 1 may be so configured that the inside of the filter unit may be invisible from outside by attaching labels on the filter unit 10, the suction filter 20 or the collection filter 21 and the like.

In addition, the shape of the body fluid filter unit 10 shown in FIG. 1 is not limited to a pillar, but the filter unit may be a prism, an elliptic cylinder, a cone or a prism and the like.

Figure 9:
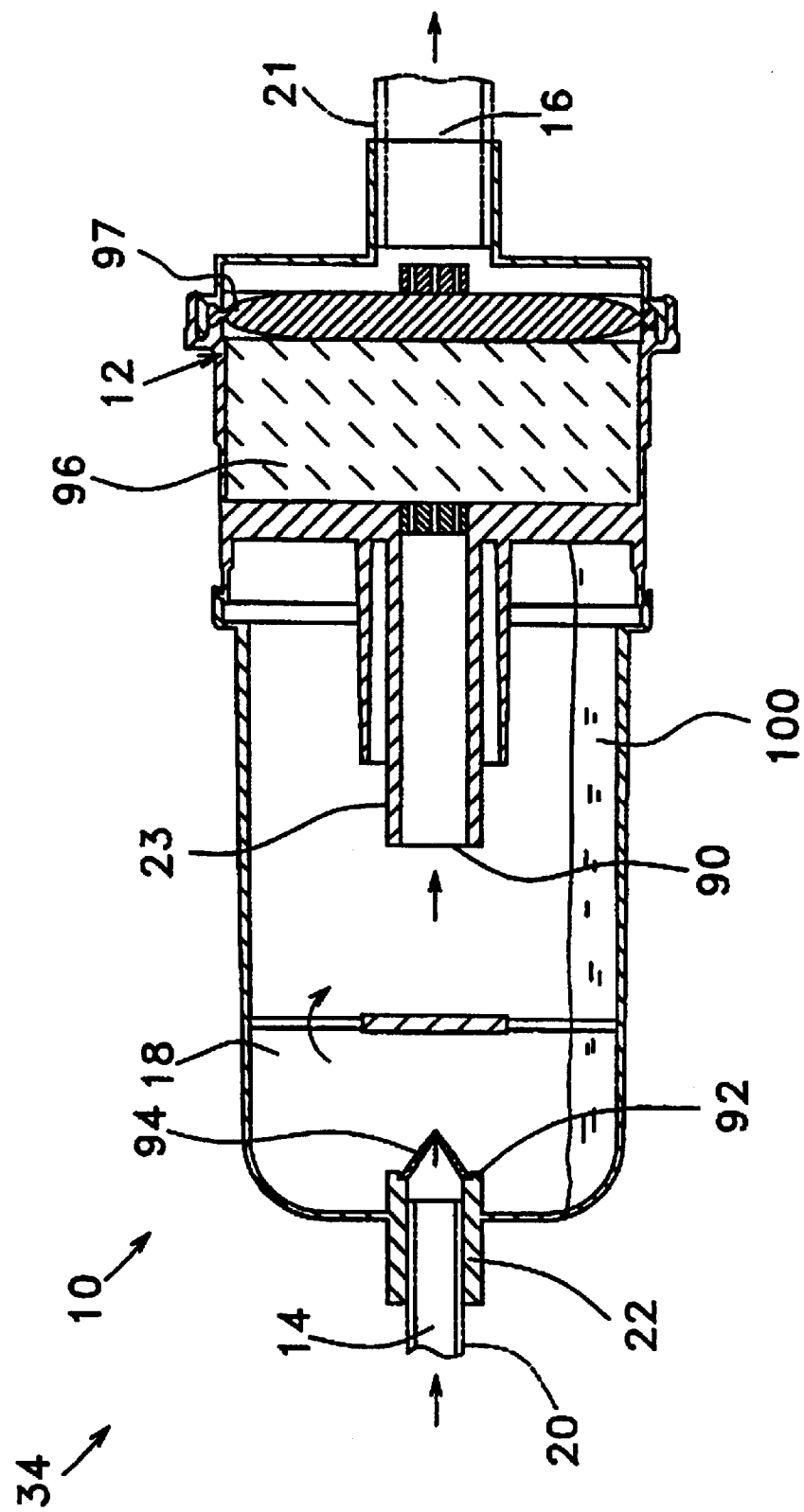
FIG. 9 is a front cross-sectional view showing another example of a filter unit according to the present invention.

The body fluid filter unit used in the present invention may be the filter unit 10 shown in FIG. 9. In the filter unit 10, the length of the jutting in the suction pipe 22 from the suction inlet 14 into the collection chamber 18 is longer than that of the filter unit 10 shown in FIG. 1. And a partition board 102 is located between the pipe 22 and the collection pipe 23. The filter unit 10 shown in FIG. 9 has, therefore, a more complicated configuration than the filter unit 10 shown in FIG. 1, which results in higher manufacturing costs than the filter unit 10 shown in FIG. 1. When this filter unit 10 is used in the position shown in FIG. 8, the body fluids 100 have more difficulties in contacting the non-return valve 94 because the length that the pipe 22 juts out of the inlet 14 into the chamber 18 is longer than the filter unit 10 shown in FIG. 1. Since the partition board 102 is located between the pipe 22 and the pipe 23, it is possible to prevent the fluids 100 emitted from the pipe 22 from being collected into the pipe 23, even if the length of the pipe 22 in this filter unit 10 that juts out of the inlet 14 into the chamber 18 is longer than the filter unit 10 shown in FIG. 1.

Figure 10:
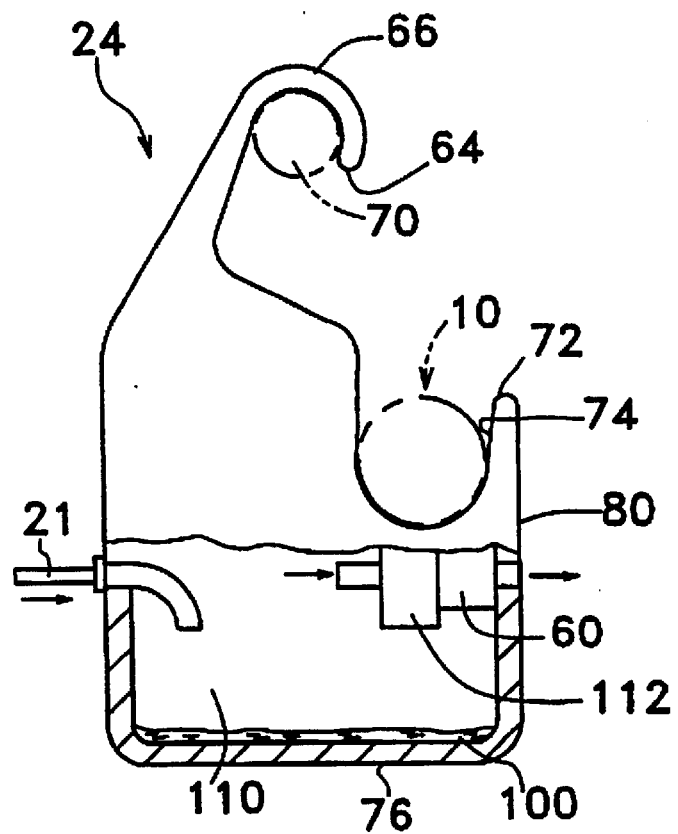
FIG. 10 is a front cross-sectional view showing another example of a suction source according to the present invention.
Figure 11:
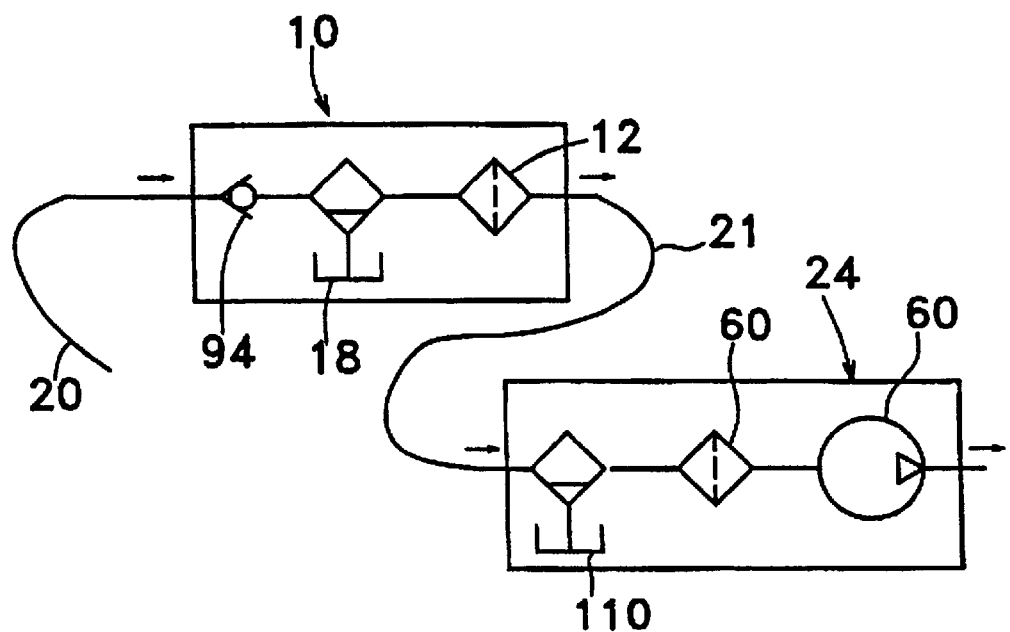
FIG. 11 is a pipe arrangement view for explaining the using condition of the suction source shown in FIG. 10.

The suction source 24 of the present invention may be either of the suction sources shown in FIGS. 10 and 11. This suction source 24 includes a filter 112 and the pump 60 within a sealed chamber 110. Even if the body fluids 100 are drawn from the collection pipe 21 into the chamber 110, only air can be fed to the pump 60 via the filter 112 by storing the body fluids 100 in the chamber 110. When fluids consisted of the fluids 100 and air are suctioned, the chamber 110 acts as a tank having a function of separating the fluids 100 from air. In the case of this suction source 24, although the complicated configuration of the suction source 24 makes the manufacturing costs high, it is possible to prevent the pump 60 from being broken down caused by admission of the fluids 100 into the pump 60.

Figure 12:
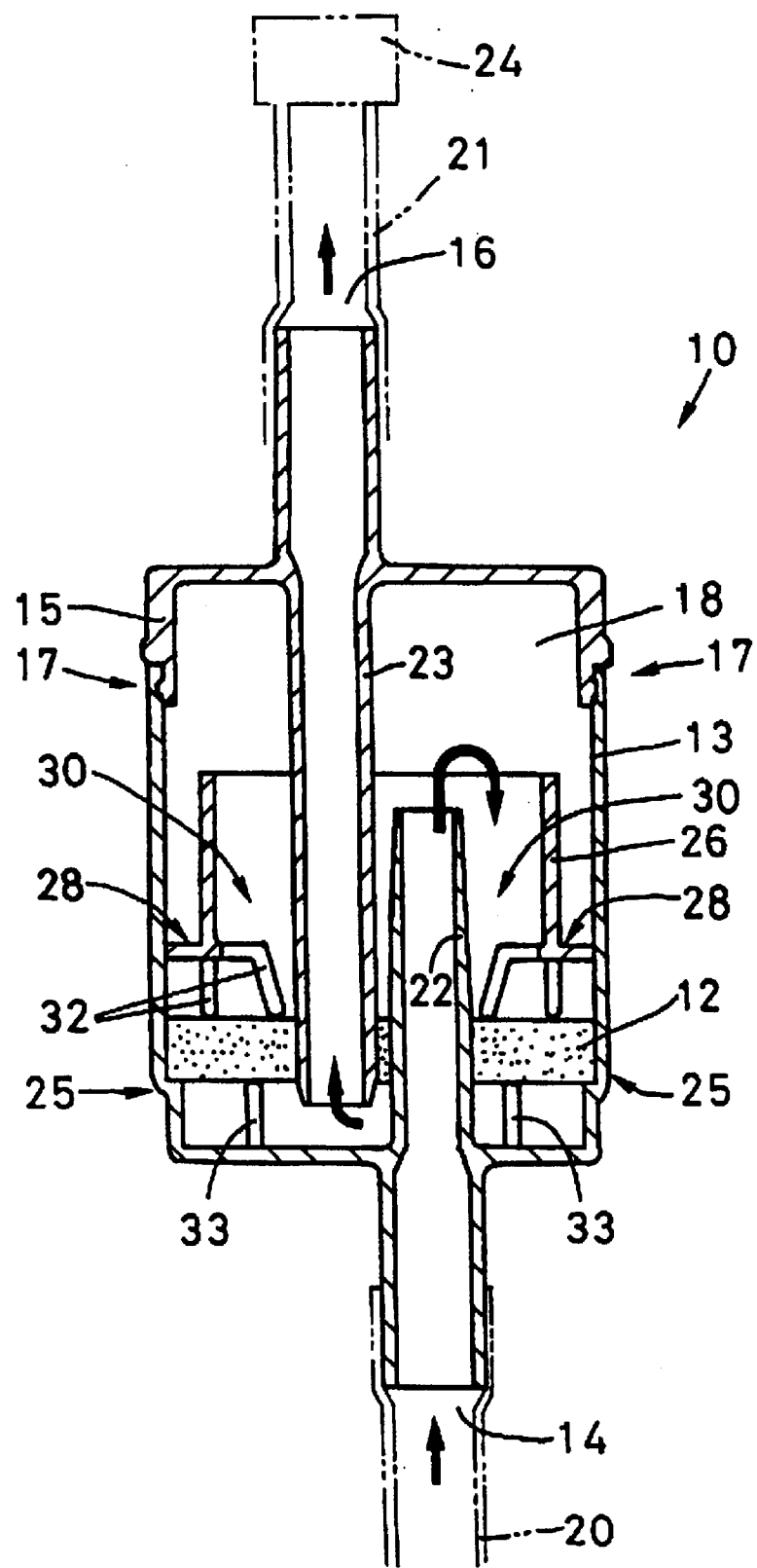
FIG. 12 is a front cross-sectional view showing still another example of a filter unit according to the present invention.

FIG. 12 shows another embodiment of the filter unit according to the present invention. The filter unit 10 shown in FIG. 12 comprises a suction inlet 14 connected to a suction tube 20 for suctioning body fluids; a collection chamber 18 for storing the body fluids sucked in together with air after separating the fluids from air; a filter 12 for allowing introduced air to pass through; and a collection inlet 16 communicating with a suction source 24. In addition, a suction pipe 22 for guiding air from the suction inlet 14 to the collection chamber 18 and a collection pipe 23 for guiding air from the chamber 18 to the collection inlet 16 are provided inside the filter unit 10, and the suction pipe 22 and the collection pipe 23 respectively pass the filter 12.

More particularly, the filter unit 10 is formed in a substantially cylindrical shape with both ends closed, wherein a female housing 13 and a male housing 15 are connected by a fit 17. And the filter 12 and a shielding member 26 are accommodated within a substantially cylindrical-shape case formed by the female housing 13 and the male housing 15.

One side of the filter 12 is supported by a step 25 disposed on sidewalls of the female housing 13 and a filter support 33 disposed at the bottom of the housing 13. The opposite side of the filter 12 is in contact with a leg 32 of the shielding member 26. The leg 32 and the filter support 33 contacting the filter 12 are formed so as to support with the respective end of the jutting portion to avoid blocking the ventilation of the filter 12.

The suction inlet 14 connected to the suction tube 20 for suctioning phlegm, or the like and the suction pipe 22 for leading from the suction inlet 14 into the collection chamber 18 are integrally provided as one component in the female housing 13, wherein the suction pipe 22 passes through the filter 12. Thus, the filter 12 is-positioned between the collection chamber 18 which is disposed on the opposite side of the inlet 14 and the inlet 14. The collection inlet 16 communicating with the suction source 24 and the collection pipe 23 led from the chamber 18 to the collection inlet 16 are disposed as one component, wherein the collection pipe 23 passes through the filter 12.

The shielding member 26 includes a shielding portion 28 whose cross section is an L-shaped circular cylinder having a shape conforming to the inner walls of the female housing 13 and the leg 32. The opened central portion of the circular cylindrical-shaped shielding portion 28 forms a ventilation section 30.

The filter unit 10 of the present invention is assembled as mentioned below. The filter 12 is pushed into the female housing 13 as far as it will go to the step 25 and the filter support 33. First, small-diameter holes are previously provided in the filter 12 to pass through the collection pipe 23 and the suction pipe 22, so that the above-mentioned work is done while passing the suction pipe 22 through these holes. Secondly, the shielding member 26 is inserted into the housing 13 to allow the leg 32 to come in contact with the filter 12. The ring shaped shielding portion 28 is fixed to a given position by fitting the shielding portion 28 into the inner walls of the housing 13.

Subsequently, the male housing 15 is allowed to come in contact with the fit 17 to connect to the female housing 13, the end portion of the collection pipe 23 is simultaneously inserted into the holes previously provided in the filter 12. The thus-assembled filter unit 10 is divided into 2 parts by the filter 12 and has a configuration so that the collection pipe 23 and the suction pipe 22 may closely penetrate the filter 12.

The filter unit 10 in this embodiment has a more complicated configuration than the body fluid filter unit 10 shown in FIG. 1, which needs more manufacturing costs than the filter unit 10 shown in FIG. 1. The filter unit in this embodiment has, however, the following effects:

The flow of air introduced by the suction source 24 passes, as the arrow's direction shows, from the suction inlet 14 to the collection chamber 18 through the suction pipe 22 and then passes through the filter 12 and the collection pipe 23 to reach the collection inlet 16. A user who is removing body fluids holds the filter unit 10 in one hand and operates the suction tube 20 by the other hand to put its end at the patient's throat where phlegm is caught. Phlegm is drawn out into the filter unit 10 by suctioning phlegm along the flow of air.

Although body fluids such as phlegm suctioned from the end of the suction tube 20 are drained in the collection chamber 18 after passing through the suction inlet 14 and the suction pipe 22, it is possible to avoid the body fluids overflowing from the suction pipe 22 from directly splashing on the filter 12 because the end of the pipe 22 faces the male housing 15, which is on the opposite side to the filter 12. This reduces the clogging of the filter 12 caused by body fluids. In addition, body fluids flowing along the inner walls of the female housing 13 are shielded by the shielding portion 28 due to the shielding member 26 disposed in the filter unit 10, which leads to further reduction in clogging of the filter 12. The shielding portion 28 is ring shaped which is cross-sectional L-shaped and forms ring-shape grooves with the shape of cross-sectional U, closely coming in contact with the inner walls of the female housing 13. There is no possibility of the body fluids stored in the collection chamber 18, therefore, flowing out to the filter 12 side, even if the filter unit 10 is tilted in either direction.

The filter 12 collects body fluids that have flown to the filter 12 and part of the fluids included in air within the collection chamber 18. Consequently, only purified air flows to the suction source 24 after passing through the collection pipe 23 and the collection inlet 16. Since the ends of the filter 12 tightly come in contact with the inner walls of the female housing 13 and the collection chamber 18 is sealed, any rough handling does not cause a leakage of the body fluids out to the collection inlet 16.

This enables the filter unit 10 of the present invention to be easily used as a disposable unit. There is a low possibility of the entire surface of the filter 12 being clogged because the ventilation section 30 is provided in the central portion of the shielding member 26 and the both sides of the filter 12 are sufficiently opened widely. Further, the suction source 24, which is relatively weak to the extent that it is used for suctioning body fluids by the user's mouth, can be used due to small pressure loss when passing through the filter 12.

In the filter unit 10 of this embodiment, the filter 12 is positioned between the suction inlet 14 and the collection inlet 16. For example, the filter unit 10 is very convenient when used as a first-aid suction device for suctioning body fluids by the user's mouth for home use. More particularly, a user can operate the suction tube 20 connected to the inlet 14 located on the lower part while holding the collection inlet 16 in his or her mouth and peeping into the patient's throat from above, which leads to especially excellent operability. Since the suction tube 20 can be shortened because of very close clearance between the inlet 14 and the throat, or the like, operate time can be reduced by quickly sucking phlegm up to the filter unit 10. Thus, it is possible to take some of the load off the patient whose phlegm is caught, as well as the user's load.

Figure 13:
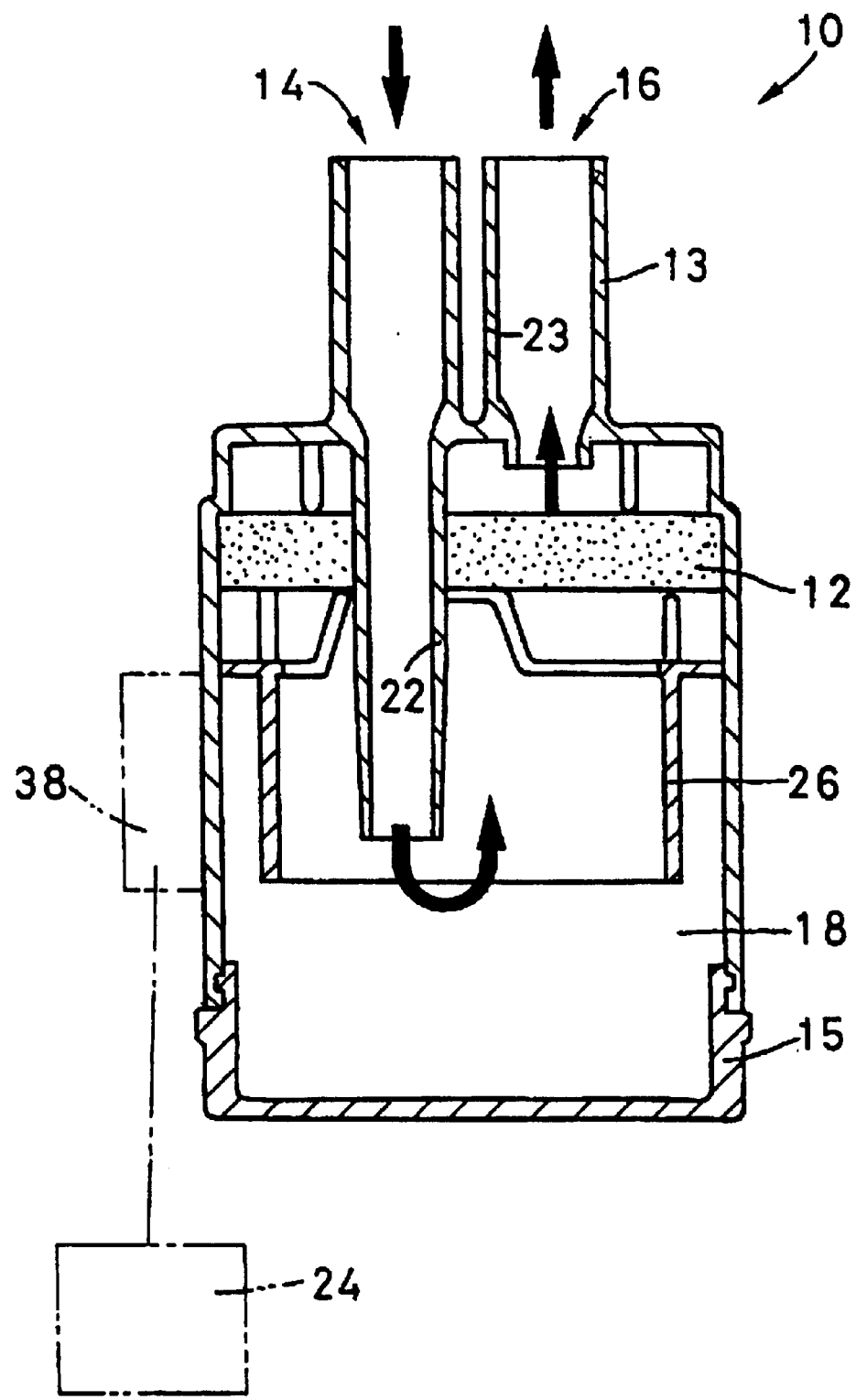
FIG. 13 is a front cross-sectional view showing a further example of a filter unit according to the present invention

The suction inlet 14 and the collection inlet 16 are provided on the same side in the filter unit 10 of another embodiment shown in FIG. 13. In this embodiment, the passing of the suction pipe 22 through the filter 12 prevents body fluids flowing out to the collection chamber 18 from directly contacting the filter 12. The body fluids flowing to the filter 12 by passing along the inner walls of the female housing 13 are blocked due to the shielding member 26 provided in the filter unit 10. This filter unit 10 shown in FIG. 13 is different from the filter unit 10 shown in FIG. 12 in simply directing air that has passed through the filter 12 to the collection inlet 16 provided in the same direction as the suction inlet 14.

The filter unit 10 in this embodiment is particularly suitable when using the suction source 24 such as a vacuum pump. When the suction source 24 such as a vacuum pump is used, switching operation is required for operating or canceling the suction source 24. In addition, suction work should be temporarily canceled-due to inability of the operation of the suction source 24 because the filter unit 10 is held in one hand and the suction tube 20 is handled by another hand. As shown in FIG. 13, however, if a switch 38 of the suction source 24 is mounted on the sidewalls of the filter unit 10 to operate the switch 38, gripping the filter unit 10, cancellation of suction work is not necessary because another hand is available at any time.

Figure 14:
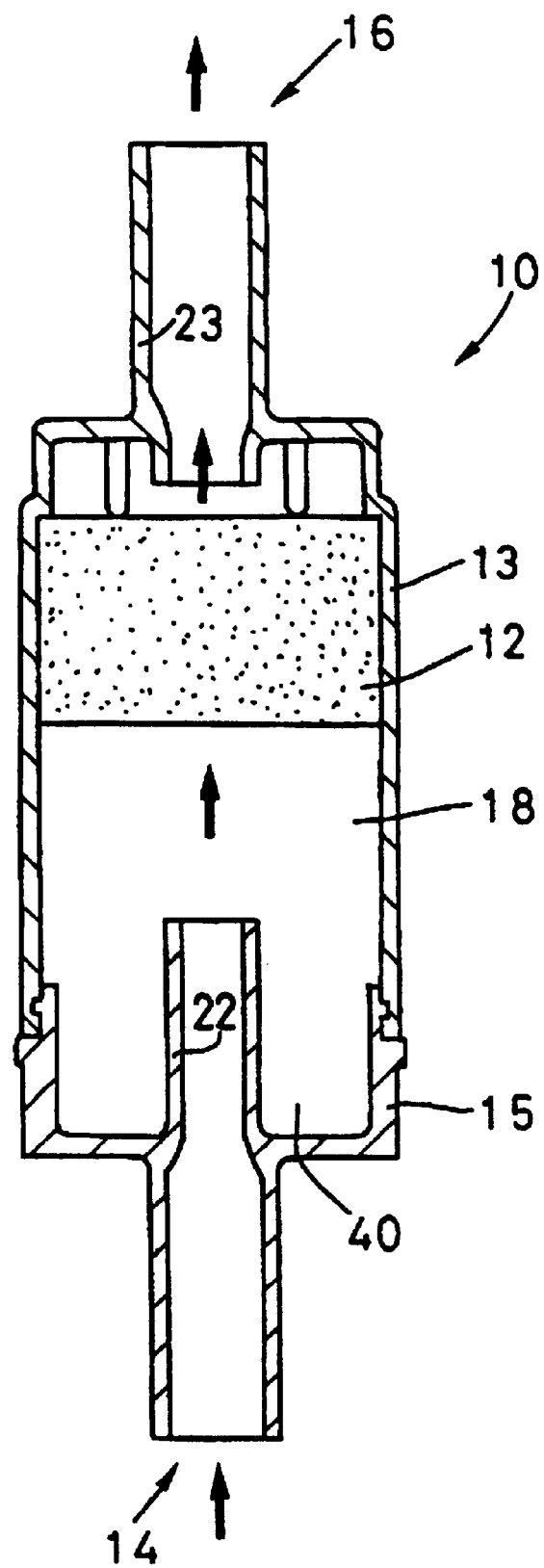
FIG. 14 is a front cross-sectional view showing a still further example of a filter unit according to the present invention

The filter unit 10 illustrated in FIG. 14 is so simply configured that the suction inlet 14, the collection chamber 18, the filter 12, and the collection inlet 16 may be disposed in series. This filter unit 10 is particularly for home use and is small sized, lightweight, and inexpensive, which is used for a suction device for suctioning body fluids by the user's mouth. More particularly, the shielding member 26 is omitted, assuming that filter unit 10 is used in the state that the suction inlet 14 faces downward by making the filter unit 10 slender because of serial disposition of the suction inlet 14, the collection chamber 18, the filter 12, and the collection inlet 16. This enables a small sized and lightweight filter unit, which results in a drastic reduction in costs. As the filter unit 10 becomes slenderer, the unit 10 is clogged more easily due to a reduction in effective area. Body fluids in the chamber 18 are, however, stored at a bottom section 40.of the male housing 15 within the chamber 18, so that there is no possibility of the body fluids drawing into the filter 12 side, unless the filter unit 10 is reversed. Moreover, the filter 12 is thickened to improve protection against clogging.

Figure 15:
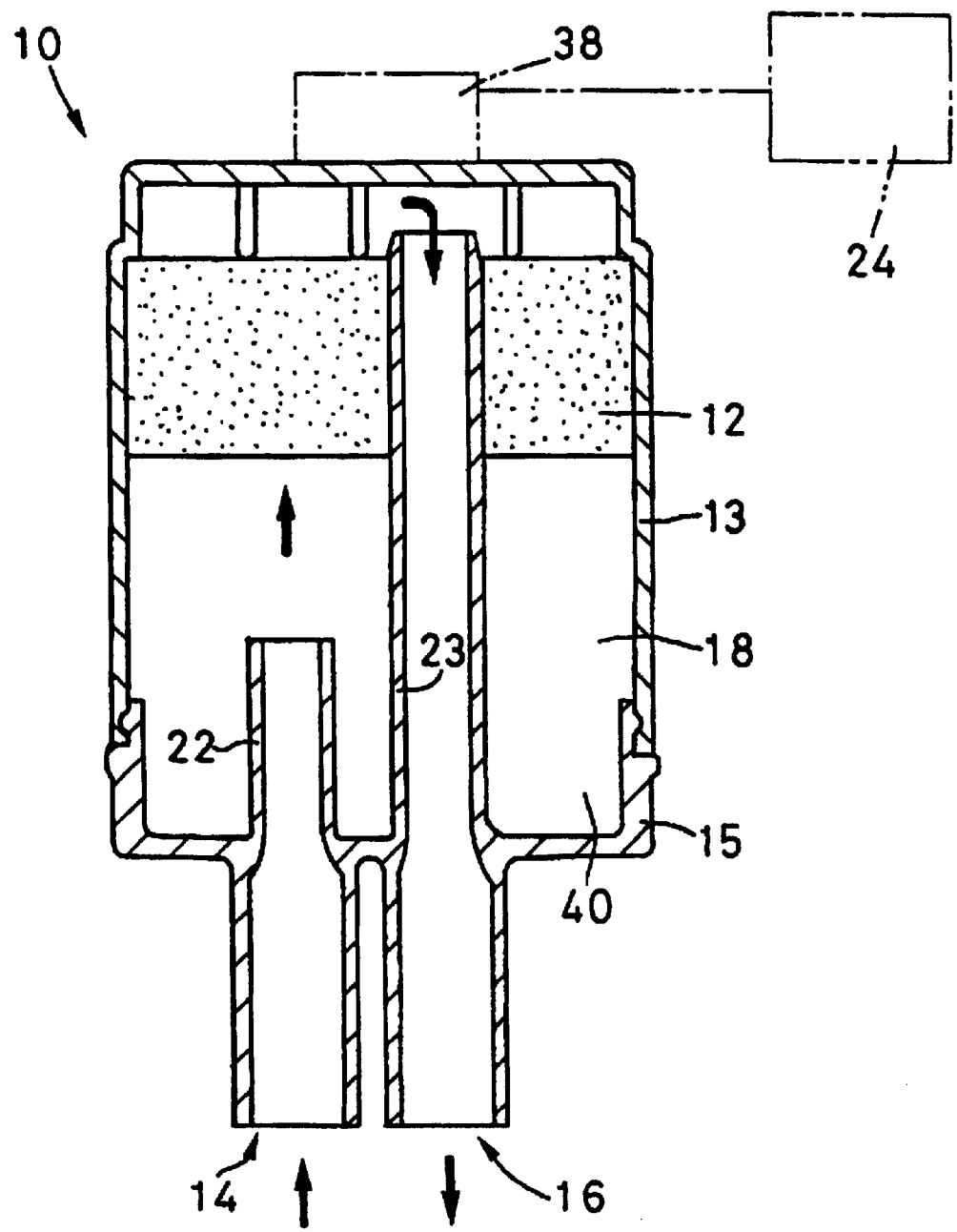
FIG. 15 is a front cross-sectional view showing another example of a filter unit according to the present invention.

In the filter unit 10 illustrated in FIG. 15, the suction inlet 14 and the collection inlet 16 are provided adjacent to each other. The filter unit 10 is particularly suitable when using the suction source 24 such as a vacuum pump as well as the filter unit 10 shown in FIG. 13. This filter unit 10 has a characteristic that the filter unit 10 is operable, for example, with a thumb by gripping it in the direction shown in FIG. 13 and mounting the switch 38 on its upper part. Since the filter 12 is positioned above the collection chamber 18, the shielding member 26 is omitted because there are few possibilities of the body fluids overflowing from the suction pipe 22 making contact with the filter 12.

As has been described so far, it becomes possible to prevent the filter unit 10 being clogged by allowing the body fluids splashed out from the suction pipe 22 to directly come in contact with the filter 12, if the pipe 22 passes through the filter 12. The filter unit 10, whose usage is limited so that the filter 12 may be located above the collection chamber 18, has, however, a low risk of the fluids splashing upward by working against gravity. It is, therefore, not always necessary for the pipe 22 to pass through the filter 12.

Further, as has been described so far, the shielding member 26 shields the flow of the body fluids flowing along the male housing 13, which leads to prevent the filter 12 from being clogged, even if the filter unit 10 is used in a tilted position in any directions. Since the filter unit 10, whose usage is limited so that the filter 12 may be located above the collection chamber 18, has a low risk of the body fluids drawing into the filter 12 because the body fluids are stored at the bottom section 40 of the male housing 15, it is not always necessary to provide the shielding member 26.

Although the filter unit 10 shown in FIGS. 1 to 15 is substantially cylindrical shaped, the filter unit 10 of the present invention may be in a variety of shapes, such as cone and prism. The filter unit 10 may have such a convenient configuration that the filter unit 10 is folded up when it is not in use and is assembled when used.

Figure 16:
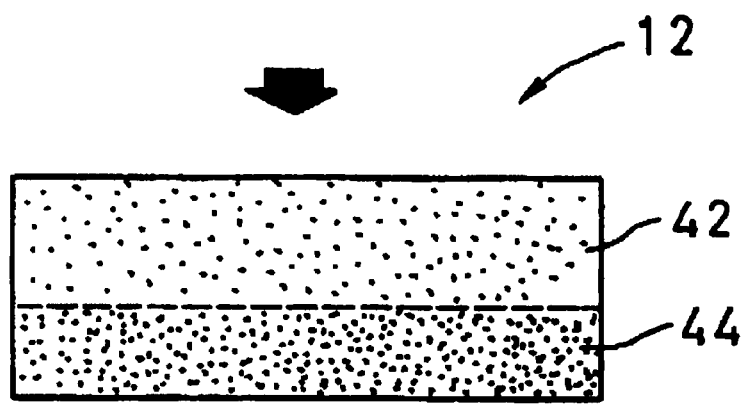
FIG. 16 is a front cross-sectional view exemplifying a filter according to the present invention.
Figure 16:
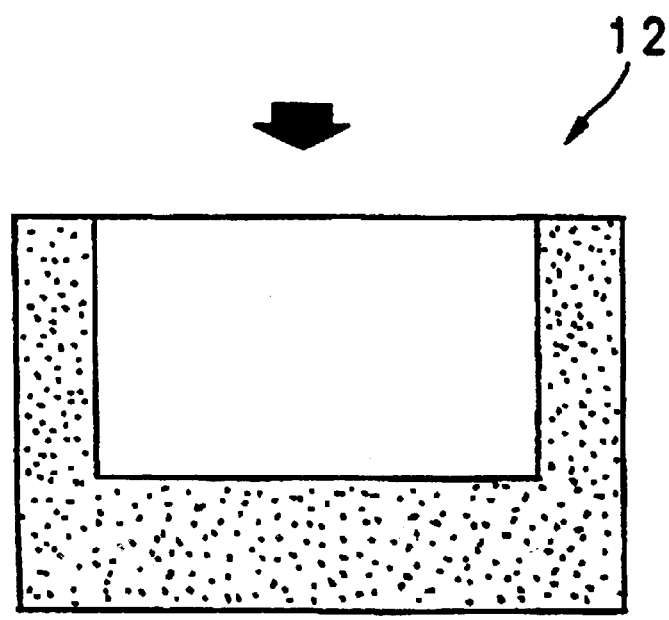
Figure 17:
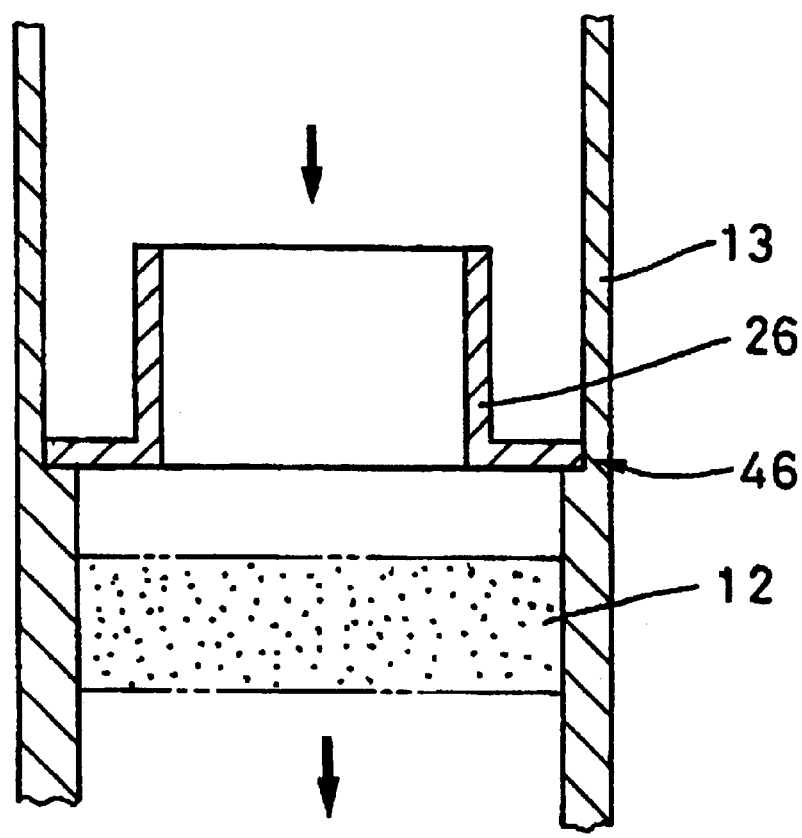
FIG. 17 is a front cross-sectional view showing an example of a shielding member according to the present invention.

The shape and the configuration of the filter 12 are not limited to the examples shown in FIGS. 1 to 15. For example, the filter 12 shown in FIG. 16 comprises two layers; a relatively rough and bulky filter material 42 and a relatively fine filter material 44. The filter material 42 is used to mainly collect body. fluids with high viscosity and the filter material 44 is used to collect the remaining body fluids with low viscosity. The filter 12 shown in FIG. 16 may be used having a configuration of three layers, or the like in accordance with its purpose. The filter 12 shown in FIG. 17 is of a shape having the circular base with sidewalls jutting to prevent the filter 12 from being clogged due to the expansion of the surface area for ventilation. Various thoughts such as expanding the surface area by attaching plaits can be adopted.

The shape and the shielding method of the shielding member 26 are not limited to the above-mentioned examples. For example, the shielding member 26 shown in FIG. 15 is aligned by being located on a step 46 disposed on the female housing 13 to shield the filter 12 at predetermined intervals without the leg 32. Accordingly, the surface of the filter 12 is perfectly opened without anything to come in contact with, so that the filter function is retained.

Figure 18:
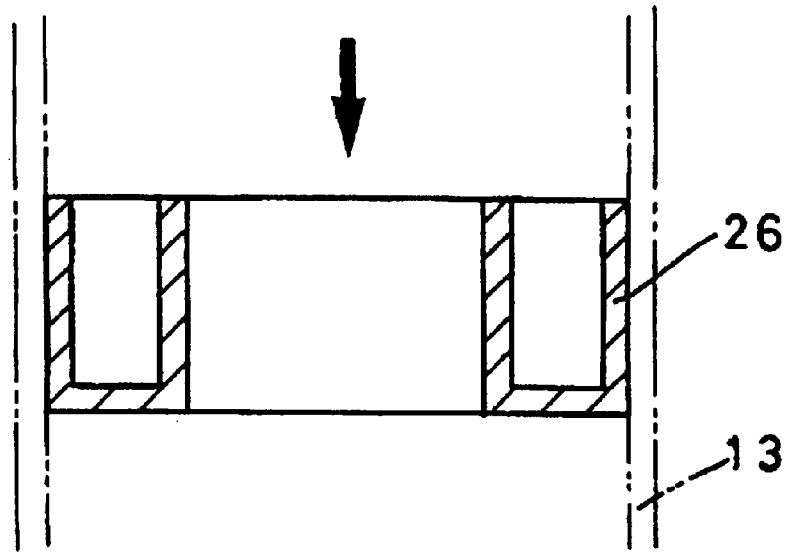
FIG. 18 is a front cross-sectional view showing another example of a shielding member according to the present invention.

Alternatively, the shielding member 26 shown in FIG. 18 is a cylindrical shape by forming grooves whose cross section is U-shaped and has a characteristic of easy assembling work of the filter unit 10 due to smooth sliding movement conforming to the inner walls of the female housing 13.

Figure 19:
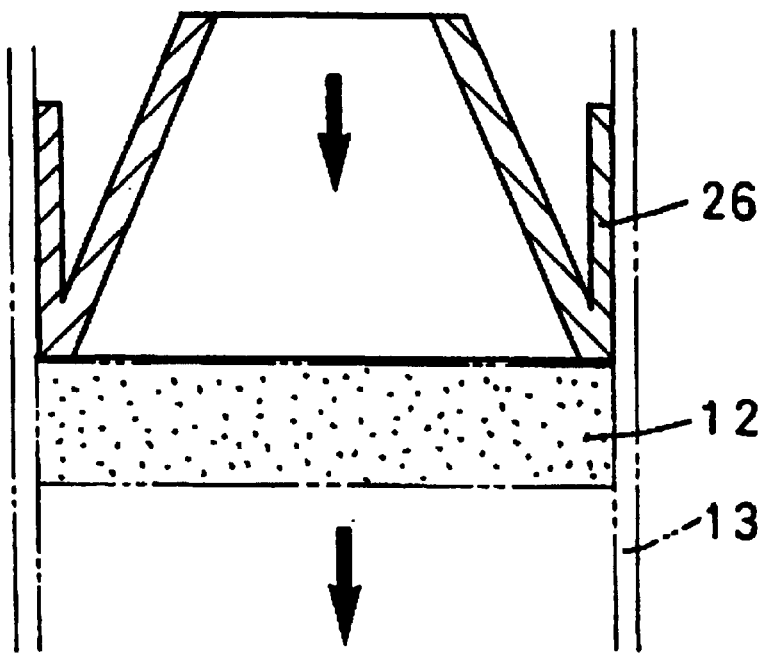
FIG. 19 is a front cross-sectional view showing still another example of a shielding member according to the present invention.

Alternatively, the shielding member 26 formed in the broadened shape shown in FIG. 19 comes in contact with only the filter 12 and its perimeter, therefore, the effective area of the filter 12 is hardly changed.

A contrivance to prevent body fluids sucked up to the collection chamber 18 from clogging the filter 12 has been carried out by allowing the suction pipe 22 to pass through the filter 12 and disposing the shielding member 26. To prevent further clogging of the filter 12, members for suctioning liquid may be provided within the collection chamber 18. In the filter unit 10 shown in FIG. 20, members 48 for suctioning liquid are disposed along the inner walls of the female housing 13. This prevents body fluids from moving to the filter 12 by absorbing water to increase viscosity and reducing body fluidity. High polymer absorbent materials and felt are used as the members 48 for suctioning liquid.

The material of the filter 12 is not particularly limited, but an air filter made of paper, a cloth, and an unwoven cloth, and the like which are ordinarily used for a ventilating opening, a dust collector, and a vacuum cleaner is preferably used. Above all, the air filter made of an unwoven cloth is the most favorably used because of little possibility of clogging due to being bulky, excellent workability in working to the optimum shape for its excellent formability and its relatively inexpensive price. If an unwoven cloth composed of organic fibers, such as polyester fiber, polypropylene fiber, and polyacrylic fiber is used for the air filter, the filter can be incinerated without contamination of the environment after use. The filter 12 may have functions, such as disinfection, sterilization, deodorant, and deodorization. The filter 12 whose color and shape may be changed according to the contents of body fluids. It is, however, difficult for the filter 12 to perfectly collect all kinds of bacteria and virus, so that the user is recommended to seek full guidance from a medical specialist when using the filter unit 10 by suctioning body fluids by the user's mouth.

A plastic such as polypropylene, ABS resin, and polycarbonate is preferably used as the material of the female housing 13, the male housing 15, and the shielding member 26. This material is lightweight, excellent in formability, and low in costs. In addition, this material enables easy observation of body fluids within the filter unit 10 because of its excellent transparency, as well as reusing combustion heat because the female housing 13 and the male housing 15 can be incinerated together with the filter 12. The material having functions, such as disinfection, sterilization, deodorant, and deodorization may be used or the material may be added.

Figure 21:
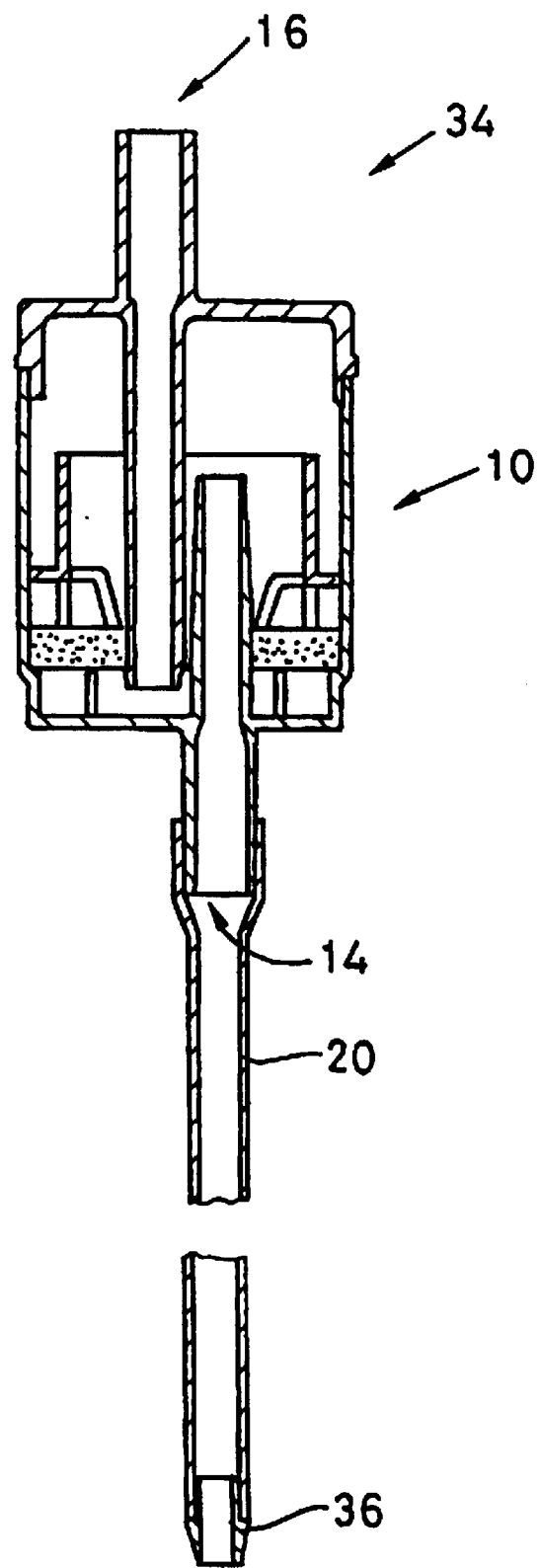
FIG. 21 is a cross-sectional view showing an example of a body fluid suction device according to the present invention.

The body fluid suction device according to the present invention includes the above-mentioned filter unit 10, wherein the suction tube 20 is connected at least to the suction inlet 14. A body fluid suction device 34 illustrated in FIG. 21 is so configured that the suction tube 20 is connected to the suction inlet 14 of the filter unit 10 shown in FIG. 12 and a nozzle 36 is connected to the end of the suction tube 20. The tube 20 is made of silicone rubber and soft polyolefin-type resin, which easily bends because of its superior flexibility.

The body fluid suction device 34 in this embodiment is used as follows: The user holds the filter unit 10 by gripping it in his or her hand and catches hold of near the end of the suction tube 20 by another hand, and allows the nozzle 36 to contact the body fluid surgical site such as a throat. Body fluids such as phlegm are aspirated and removed by holding the collection inlet 16 in his or her mouth to aspirate the fluids. Alternatively, the suction device 34 may be used as follows: the user holds the filter unit 10 by holding the collection inlet 16 in his or her mouth and operates the suction tube 20 intensively by both hands. The suction device 34 may be used by communicating the collection inlet 16 with the suction source 24 such as a vacuum pump through a collection tube and the like. When the suction source 24 such as a vacuum pump is used, some degree of vacuum adjusting means is preferably disposed between the collection inlet 16 and the suction source 24.

The body fluid suction device 34 of the present invention is easily portable due to the use of the small sized and lightweight filter unit 10. Particularly, in the system of suctioning body, fluids by the user's mouth, it is very convenient to use the suction device 34 for ordinary home use and medium or small sized medical facilities because of no need of the suction source 24 such as a vacuum pump. If the collection inlet 16 is of a shape for holding in the user's mouth, the suction device 34 is particularly useful because the user holds the filter unit 10 in his or her mouth and operates the suction tube 20 and helps the patient by his or her free hands.

The body fluid suction device 34 of the present invention can solve hygienic and mental problems raised in conventional suction devices because there is no risk of body fluids drawing into the user's mouth due to complete removal of the body fluids such as phlegm using the filter 12, even if the user suctions the body fluids by his or her mouth. Since the suction device 34 that has been used is disposed of as it were, no troublesome work, such as cleaning and disinfection is required. The suction device 34 to be disposed of can be perfectly incinerated, so that its combustion heat may be reused. If the filter unit 10, the suction tube 20, and the nozzle 36, or the like, are made of polyolefin-type resin, little toxic gas is caused by incineration.

Figure 22:
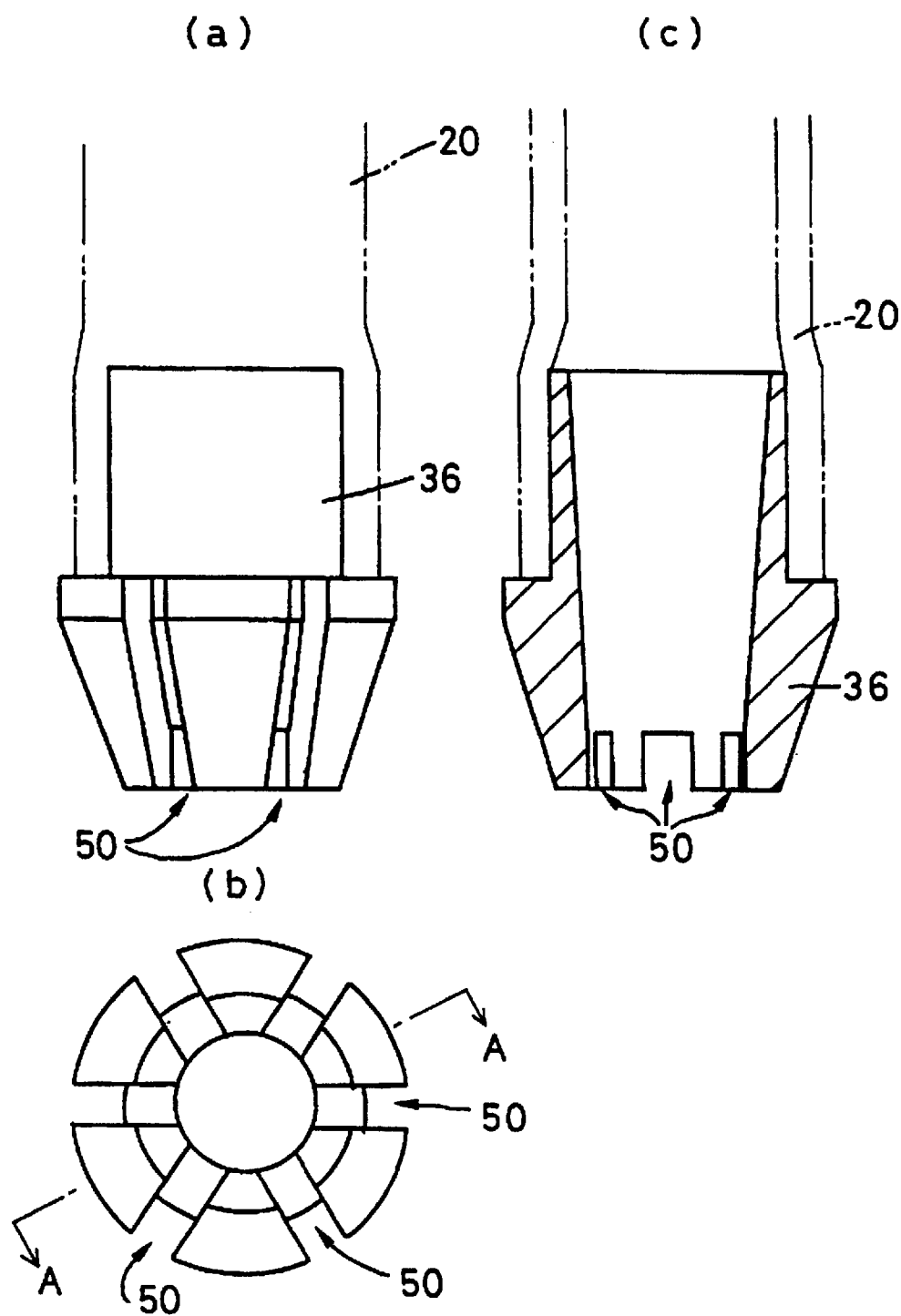
FIG. 22 is an example of a nozzle according to the present invention.

The nozzle 36 serves to prevent the end of the suction tube 20 from being adhered to the inner surface of the user's mouth due to the blocking and adsorption. FIG. 22 shows an example of the nozzle 36. Grooves 50 for drilling an end surface and sides are provided at 6 places of the end of the nozzle 36 to be configured so as to introduce air from the sides, even if the end surface is blocked. More particularly, the nozzle 36 has an air inhalation system. Thus, for example, even when the nozzle 36 is blocked by coming in touch with the inner surface of the user's mouth during suctioning of phlegm, air is introduced from the sides through the grooves, which results in no reduction in flow rate of carried air within the suction tube 20 without the anchoring of the end in the inner surface of his or her mouth and comfortable suctioning. The nozzle 36 suitable for the shape of nostrils is preferably used when suctioning nasal mucus, or the like. The nozzle 36 is, however, not always necessary in a usage wherein the end of the suction tube 20 is seldom blocked.

Figure 20:
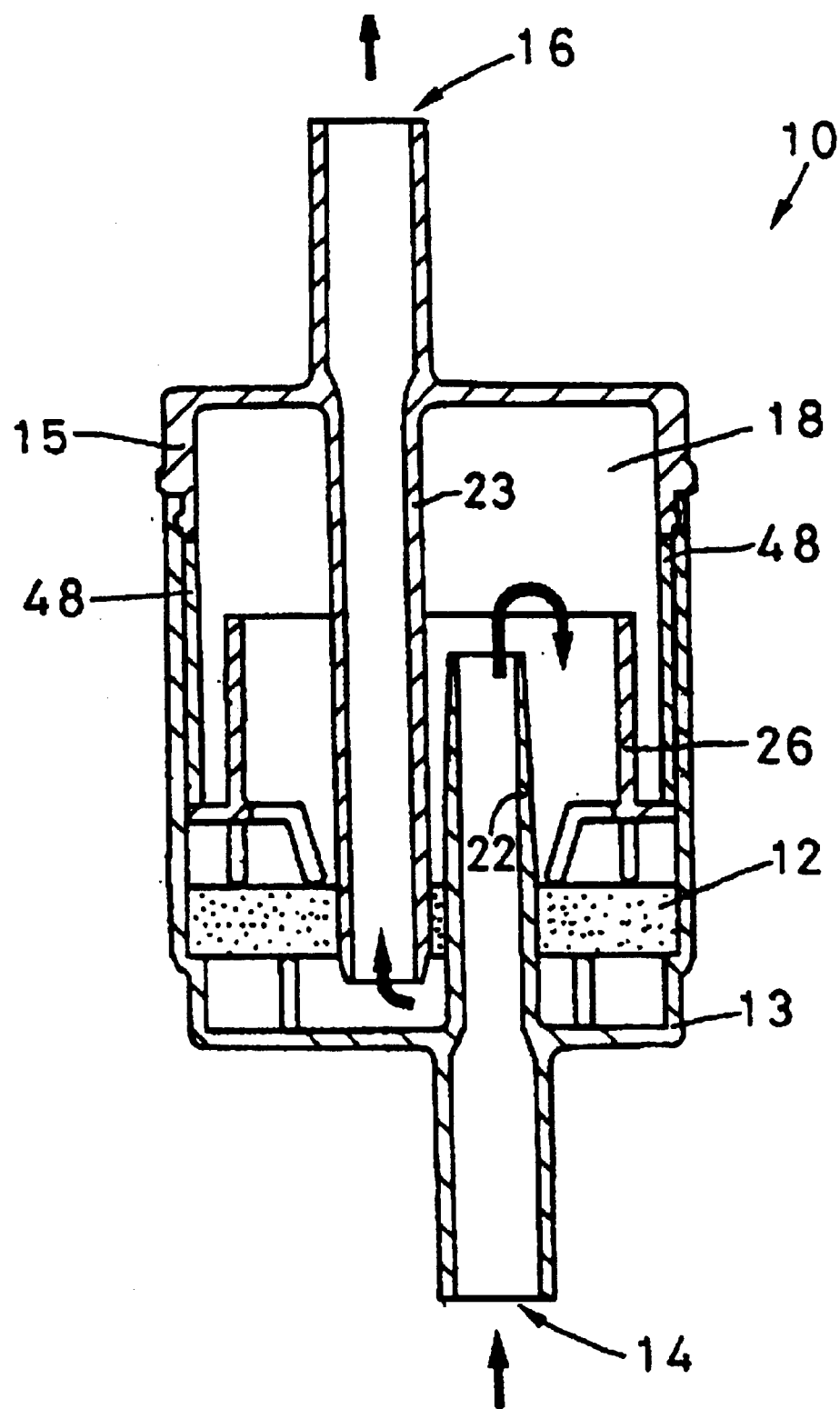
FIG. 20 is a front cross-sectional view showing still another example of a filter unit according to the present invention.
Figure 23:
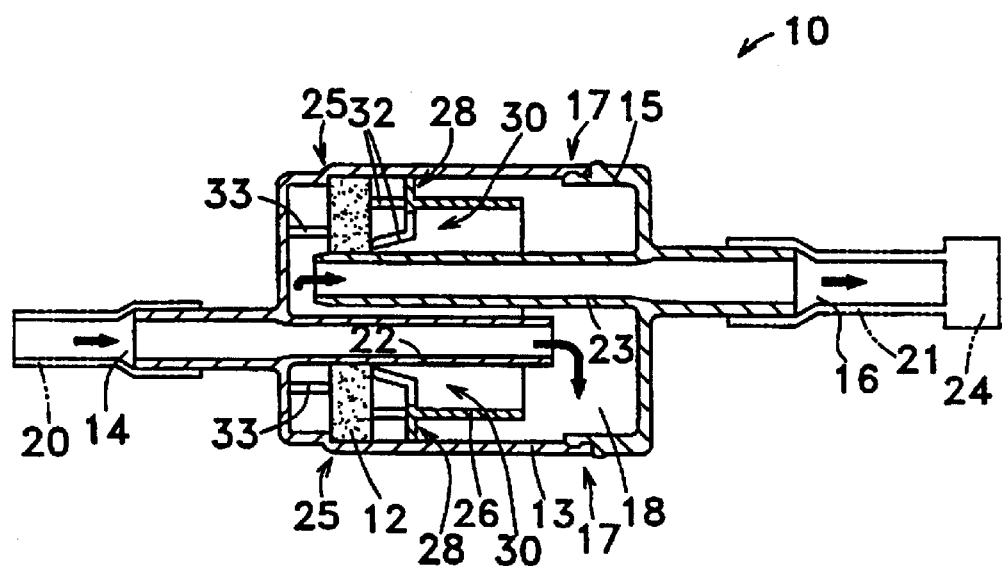
FIG. 23 is a cross-sectional view showing the using condition of the filter unit shown in FIG. 12.
Figure 24:
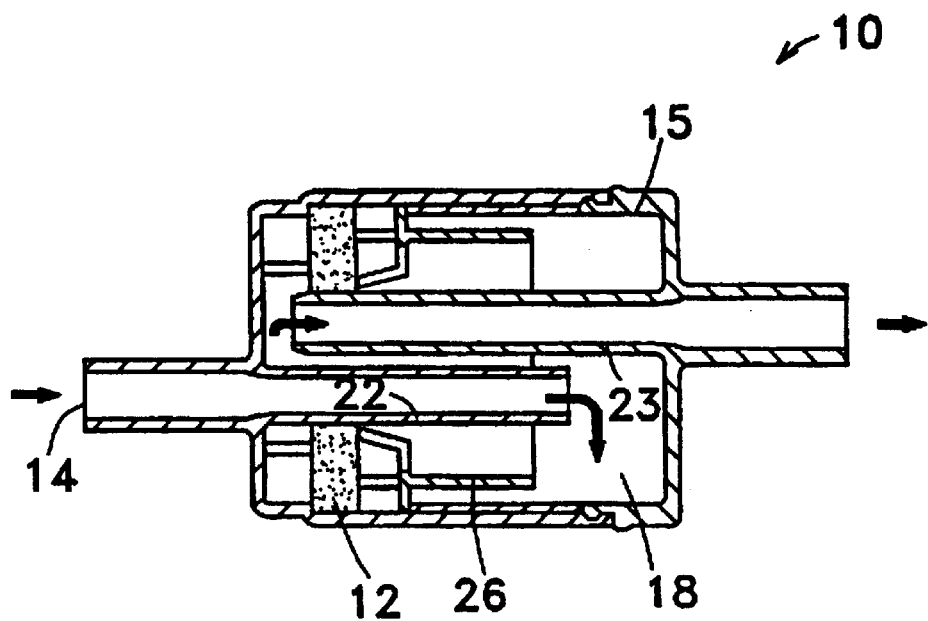
FIG. 24 is a cross-sectional view showing the using condition of the filter unit shown in FIG. 20.
Figure 25:
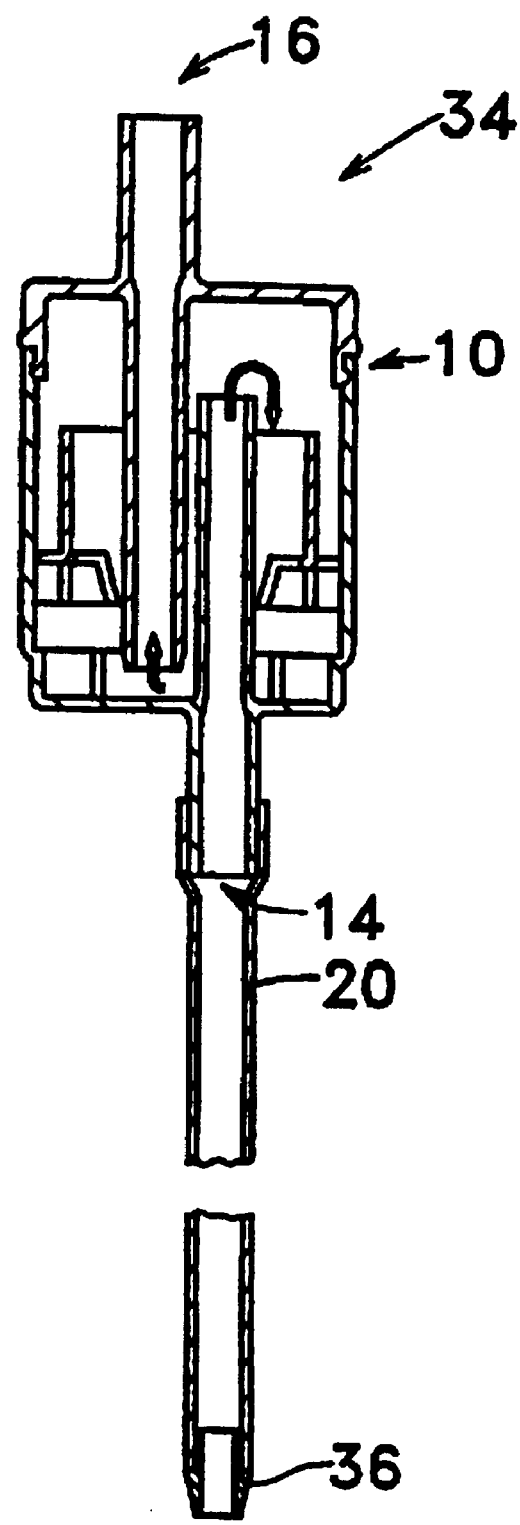
FIG. 25 is a cross-sectional view showing the using condition of the filter unit shown in FIG. 21.

The body fluid filter unit 10 shown in FIG. 12 is preferably used sideways in the configuration as shown in FIG. 23. And the body fluid filter unit 10 shown in FIG. 20 is preferably used sideways as shown in FIG. 24. The body fluid filter unit 10 shown in FIG. 21 is preferably used sideways in the configuration was shown in FIG. 25. The body fluid filter unit 10 respectively shown in FIGS. 13, 14, and 15 may be used sideways.

As described above, the disposable body fluid filter unit and the body fluid suction device according to the present invention have been described in detail so far, but the present invention is not limited to the above-mentioned embodiments. Also, any modification, variations or equivalent arrangement on the shape, material, and configuration of the filter unit and the filter, and the configuration of the body fluid suction device and the like, which may occur to those skilled in the art, should be considered to be within the scope of the invention.

INDUSTRIAL APPLICABILITY

The disposable body fluid filter unit according to the present invention does not allow foul air to flow into a suction source such as a mouth because a filter and a shielding member collect body fluids such as phlegm removed by suctioning. In addition, there are no changes in its filter functions even when the filter unit is tilted or overturns, so that the filter unit can be easily used.

Further, the body fluid filter unit according to the present invention is free from troublesome work, such as cleaning and disinfection due to being a disposable type.

Furthermore, such body fluid filter unit can prevent overflowing body fluids from a suction pipe from being clogged by directly splashing on the filter by providing a suction pipe for guiding air from a suction inlet to a collection chamber which passes through the filter.

Additionally, the body fluid filter unit has particularly superior operability because a user can use a suction tube connected to the suction inlet positioned on the lower part while holding a collection inlet in his or her mouth and peeping into the patient's throat from above, if the filter can be positioned between the suction inlet and the collection inlet. Also, operation time is reduced by the suction tube shortened by an approach of the suction inlet to the operation site such as the throat and quick suction of phlegm, or the like up to the filter unit. This also reduces some of the load off the patient whose phlegm is caught in person's throat and nose, as well as the user's load.

Moreover, with the use of the body fluid filter unit according to the present invention, the flowing of body fluids into the inner walls of a case is blocked, if a shielding member having a body fluid shielding portion in the shape being in conformance with the shape of the inner walls of the collection chamber disposed around the shielding member and a ventilation section formed near the central portion, is provided between the collection chamber and the filter. This reduces clogging in the filter.

The body fluid filter unit according to the present invention comprises a suction inlet connected to a suction tube for suctioning body fluids; a collection chamber for storing body fluids suctioned from the suction inlet; a filter for allowing air or body fluids within the collection chamber to pass through; a collection inlet communicating with a suction source, wherein the suction inlet is positioned at one end of the collection chamber and the collection inlet is positioned at the other end that is opposite to the one end, and the filter is positioned between the collection chamber and the collection inlet. Unlike a body fluid filter unit for giving suction generated from a collection pipe to a filter through a specified chamber, the body fluid filter unit of the present invention allows air to effectively pass through the filter by resisting fluid friction because its suction generated from the collection pipe is directly given to the filter. This enables introduction of air with less suction, which leads to a reduction in electricity cost of a suction source, compared with the filter unit for giving suction generated from a collection pipe to a filter through the specified chamber. In addition, the suction source can be configured in a compact size.

There is no possibility of body fluids drawing into the collection pipe, as far as the amount of the body fluids is not too large, even if the body fluid filter unit according to the present invention is used in any postures, wherein the collection pipe for guiding air from the collection chamber to the collection inlet through the filter is provided and juts into the collection chamber. Particularly, with the use of the body fluid filter unit of the present invention having the collection pipe jutting out of the filter into the central portion of the collection chamber, wherein the end of the jutting portion is positioned near the central portion of the collection chamber, there is no risk of the body fluids drawing into the collection pipe, unless the capacity of the fluids stored in the collection chamber reaches half of that of the collection chamber or more. This prevents the fault of the suction source caused by the body fluids drawn into the suction source. Additionally, it becomes possible to suction body fluids by the user's mouth from the collection tube connected to the collection inlet.

The body fluid filter unit according to the present invention having a suction pipe for guiding body fluids from the suction inlet to the collection chamber can prevent the body fluids from returning by surely guiding the fluids fed to the filter unit to the collection chamber. This enables effective suctioning of body fluids. As far as the amount of body fluids stored in the collection chamber is not too large, the filter unit with a suction pipe jutting into the collection chamber according to the present invention can particularly prevent the body fluids from returning to the suction pipe more surely because the body fluids do not contact the end of the jutting portion of the suction pipe, even if the filter unit is used in any postures. Particularly, in the filter unit having a non-return valve on the end of the jutting portion of the suction pipe according to the present invention, there is no possibility of the body fluids returning to the suction pipe, even though the body fluids contact the end of the jutting portion of the suction pipe.

The body fluid filter unit of the present invention whose collection chamber is small enough to conceal in a palm of a human hand does not give the patient and the caregiver any unpleasant feelings due to invisible body fluids in the collection chamber from the outside.

The present invention can provide a disposable body fluid suction device that is easily portable due to its small sized and lightweight filter unit. Particularly, if the suction device has a system of suctioning body fluids by the user's mouth, the suction device is very conveniently used as a first-aid treatment in ordinary home and caregivers without any suction source such as a vacuum pump because there is no need of a suction source such as a vacuum pump. Additionally, if the suction inlet is of a shape for holding in the user's mouth, it becomes particularly useful because the user holds the filter unit in his or her mouth, so that he or she can operate the suction tube or can help the patient by his or her both free hands.

The body fluid suction device of the present invention can solve hygienic and mental problems raised in conventional suction devices because there is no risk of body fluids drawing into the user's mouth due to complete removal of the body fluids such as phlegm by the filter unit, even if the user suctions the fluids by his or her mouth. Since the suction device that has been used is disposed of as it were, no troublesome work, such as cleaning and disinfection is required. The suction device to be disposed of can be perfectly incinerated. Unless vinyl chloride resin is used as the material of the filter unit, little toxic substance such as dioxin is caused by incineration, so that its combustion heat may be reused.

Further, connecting a nozzle including an air inhalation system to the end of the suction tube prevents the end from being adhered to the inner surface of the user's mouth and the like due to adsorption, so that its operability is improved.

The body fluid suction device of the present invention is mainly used to remove body fluids such as phlegm and nasal mucus by exercising the above-mentioned various effects. The suction device may be used as a collection chamber to store by the time of testing body fluids to be suctioned which does not need to be displaced. and in cleaning an external ear related disease, or the like.

The present invention can provide a suction source wherein an outer box can be suspended by engaging a curved hook extending to an end with a bar-like member. Fixing the suction source to the fence of the bed can perform suctioning operation. Accordingly, space of the patient room can be effectively utilized.

The suction source of the present invention has an outer box having a curved mounting section extending to an end where the substantially cylinder-shape body fluid filter unit is accommodated on its side. Fixing the filter unit to the suction source can perform suctioning operation. Accordingly, space of the patient room can be effectively utilized.

Furthermore, the suction source of the present invention including a tank for dividing suctioned fluids into body fluids and air can feed only air to a pump within the suction source, which results in no fault in the pump, even though the body fluids draw into the suction source.

What is claimed is:

1. A disposable body fluid filter unit for removing body fluids such as phlegm and nasal mucus caught in person's throat and nose, the improvement wherein said filter unit is so configured that air flows through a suction inlet connected to one end of a suction tube for suctioning the body fluids, a collection chamber, a filter, and a collection inlet communicating with a suction source, in the order named, to suction the body fluids, and wherein a suction pipe for guiding air from the suction inlet to the collection chamber passes through the filter.

2. The filter unit according to claim 1, wherein the filter is positioned between the suction inlet and the collection inlet.

3. The filter unit according to claim 1, wherein a shielding member having a body fluid shielding portion in the shape being in conformance with the shape of inner walls of the collection chamber disposed around the shielding member and a ventilation section formed near the central portion of the shielding member is provided between the collection chamber and the filter.

4. The filter unit according to claim 1, further comprising a collection pipe for guiding air from said collection chamber to the collection inlet through the filter which juts into the collection chamber.

5. The filter unit according to claim 4, wherein said collection pipe juts out of the filter into the central portion of the collection chamber and an end of a jutting portion of the collection pipe is positioned near the central portion of the collection chamber.

6. The filter unit according to claim 1, further comprising a suction pipe for guiding body fluids from said suction inlet to said collection chamber.

7. The filter unit according to claim 6, wherein said suction pipe juts into the collection chamber.

8. The filter unit according to claim 7, wherein a jutting portion of said suction pipe has a non-return valve on its end.

9. The filter according to claim 1, wherein said collection chamber is sufficiently small to be held and enclosed in an adult person's hand.

10. The suction device according to claim 1, wherein a nozzle having an air inhalation system is connected to an opposite end of said suction tube.

11. The suction device according to claim 1, wherein said collection inlet is of a shape that allows a user to hold the inlet in his or her mouth.

12. A disposable body fluid filter unit for removing body fluids such as phlegm and nasal mucus caught in person's throat and nose, the improvement wherein said filter unit is so configured that air flows through a suction inlet connected to a suction tube for suctioning the body fluids, a collection chamber, a filter, and a collection inlet communicating with a suction source, in the order named, to suction the body fluids, and wherein a shielding member, having a body fluid shielding portion in the shape being in conformance with the shape of inner walls of the collection chamber disposed around the shielding member and a ventilation section formed near the central portion of the shielding member, is provided between the collection chamber and the filter.

13. A disposable body fluid suction device comprising:
(a) a disposable body fluid filter unit for removing body fluids such as phlegm and nasal mucus caught in person's throat and nose, wherein said filter unit is so configured that air flows through a suction inlet connected to an end of a suction tube for suctioning the body fluids, a collection chamber, a filter, and a collection inlet communicating with a suction source, in the order named, to suction the body fluids; and (b) a nozzle having an air inhalation system connected to the end of said suction tube, said air inhalation system including means for preventing the end of the suction tube from being closed to air when the body fluid suction device is used.

14. The suction device according to claim 13, wherein said collection inlet is of a shape that allows a user to hold the inlet in his or her mouth.

* * * * *